US007670279B2

(12) United States Patent
Gertner

(10) Patent No.: US 7,670,279 B2
(45) Date of Patent: Mar. 2, 2010

(54) PERCUTANEOUS GASTROPLASTY

(76) Inventor: Michael Gertner, 520 Laurel St., Menlo Park, CA (US) 94025

( * ) Notice: Subject to any disclaimer, the term of this patent is extended or adjusted under 35 U.S.C. 154(b) by 1303 days.

(21) Appl. No.: 11/125,547

(22) Filed: May 10, 2005

(65) Prior Publication Data

US 2005/0216042 A1 Sep. 29, 2005

Related U.S. Application Data

(63) Continuation-in-part of application No. PCT/US2005/009322, filed on Mar. 19, 2005, which is a continuation-in-part of application No. 10/974,248, filed on Oct. 27, 2004, now Pat. No. 7,255,675.

(60) Provisional application No. 60/556,004, filed on Mar. 23, 2004, provisional application No. 60/584,219, filed on Jul. 1, 2004, provisional application No. 60/603,944, filed on Aug. 23, 2004.

(51) Int. Cl.
*A61F 2/00* (2006.01)
(52) U.S. Cl. ........................................................ 600/37
(58) Field of Classification Search ............ 600/16–18, 600/37; 606/151, 157, 216, 232
See application file for complete search history.

(56) References Cited

U.S. PATENT DOCUMENTS

| 233,475 | A | 10/1880 | Cook et al. |
|---|---|---|---|
| 1,461,524 | A | 7/1923 | Goddard |
| 3,571,864 | A | 3/1971 | Oger |
| 3,664,435 | A | 5/1972 | Dabbs et al. |
| 4,060,089 | A | 11/1977 | Noiles |
| 4,133,315 | A | 1/1979 | Berman et al. |
| 4,246,893 | A | 1/1981 | Berson |
| 4,416,267 | A | 11/1983 | Garren et al. |
| 4,458,681 | A | 7/1984 | Hopkins |
| 4,472,226 | A | 9/1984 | Redinger et al. |
| 4,485,805 | A | 12/1984 | Foster, Jr. |
| 4,558,699 | A | 12/1985 | Bashour |
| 4,592,342 | A | 6/1986 | Salmasian |
| 4,669,473 | A | 6/1987 | Richards et al. |
| 4,694,827 | A | 9/1987 | Weiner et al. |
| 4,705,040 | A | 11/1987 | Mueller et al. |

(Continued)

FOREIGN PATENT DOCUMENTS

| WO | WO 99/25418 | 5/1999 |
|---|---|---|
| WO | WO 03/095015 | 11/2003 |
| WO | WO 2004/004542 | 1/2004 |
| WO | WO 2004/014237 | 2/2004 |
| WO | WO 2004/019765 | 3/2004 |
| WO | WO 2004/021894 | 3/2004 |
| WO | WO 2005/018417 | 3/2005 |
| WO | WO 2005/020802 A2 | 3/2005 |
| WO | WO 2006/127431 | 11/2006 |

OTHER PUBLICATIONS

Buchwald, et al., "Evolution of Operative Procedures for the Management of Morbid Obesity 1950-2000", *Obesity Surgery*, (2003) 12:705-717.

(Continued)

*Primary Examiner*—Samuel G Gilbert
(74) *Attorney, Agent, or Firm*—Knobbe Martens Olson & Bear, LLP

(57) ABSTRACT

Disclosed are methods and apparatus for implantation into the walls of an organ such as the stomach. Deformable or inflatable anchors with a connector between are used to pull the walls of the organ together, or to implant devices in the wall of the organ. Also disclosed are surgical instruments useful in practicing the disclosed methods.

18 Claims, 30 Drawing Sheets

U.S. PATENT DOCUMENTS

| | | | |
|---|---|---|---|
| 4,723,547 | A | 2/1988 | Kullas et al. |
| 4,803,985 | A | 2/1989 | Hill |
| 4,899,747 | A | 2/1990 | Garren et al. |
| 5,112,310 | A | 5/1992 | Grobe |
| RE34,021 | E | 8/1992 | Mueller et al. |
| 5,151,086 | A | 9/1992 | Duh et al. |
| 5,234,454 | A | 8/1993 | Bangs |
| 5,246,456 | A | 9/1993 | Wilkinson |
| 5,258,015 | A | 11/1993 | Li et al. |
| 5,259,399 | A | 11/1993 | Brown |
| 5,269,809 | A | 12/1993 | Hayhurst et al. |
| 5,292,344 | A | 3/1994 | Douglas |
| 5,423,872 | A | 6/1995 | Cigaina |
| 5,445,608 | A | 8/1995 | Chen et al. |
| 5,549,621 | A | 8/1996 | Bessler et al. |
| 5,601,604 | A | 2/1997 | Vincent |
| 5,634,936 | A | 6/1997 | Linden et al. |
| 5,690,691 | A | 11/1997 | Chen et al. |
| 5,888,196 | A | 3/1999 | Bonutti |
| 5,931,788 | A | 8/1999 | Keen et al. |
| 5,938,669 | A | 8/1999 | Klaiber et al. |
| 5,951,590 | A * | 9/1999 | Goldfarb ............... 606/232 |
| 5,961,440 | A * | 10/1999 | Schweich et al. ............ 600/16 |
| 5,993,473 | A | 11/1999 | Chan et al. |
| 6,013,053 | A | 1/2000 | Bower et al. |
| 6,045,497 | A | 4/2000 | Schweich et al. |
| 6,067,991 | A | 5/2000 | Forsell |
| 6,080,160 | A | 6/2000 | Chen et al. |
| 6,102,922 | A | 8/2000 | Jakibsson et al. |
| 6,113,609 | A | 9/2000 | Adams |
| 6,162,234 | A | 12/2000 | Freedland et al. |
| 6,447,533 | B1 | 9/2002 | Adams |
| 6,454,785 | B2 | 9/2002 | De Hoyos Garza |
| 6,475,136 | B1 | 11/2002 | Forsell |
| 6,491,707 | B2 | 12/2002 | Makower |
| 6,511,490 | B2 | 1/2003 | Robert et al. |
| 6,535,764 | B2 | 3/2003 | Imran et al. |
| 6,558,400 | B2 | 5/2003 | Deem et al. |
| 6,656,182 | B1 | 12/2003 | Hayhurst |
| 6,669,713 | B2 | 12/2003 | Adams |
| 6,746,460 | B2 | 6/2004 | Gannoe et al. |
| 6,755,869 | B2 | 6/2004 | Geitz |
| 6,908,487 | B2 | 6/2005 | Cigaina |
| 6,981,978 | B2 | 1/2006 | Gannoe |
| 6,994,715 | B2 | 2/2006 | Gannoe et al. |
| 7,033,373 | B2 | 4/2006 | De la Torre et al. |
| 7,037,344 | B2 | 5/2006 | Kagan et al. |
| 7,223,277 | B2 | 5/2007 | DeLegge |
| 7,310,557 | B2 | 12/2007 | Maschino et al. |
| 7,534,248 | B2 | 5/2009 | Mikkaichi et al. |
| 2001/0010005 | A1 | 7/2001 | Kammerer et al. |
| 2001/0011543 | A1 | 8/2001 | Forsell |
| 2002/0055757 | A1 | 5/2002 | Torre et al. |
| 2002/0188354 | A1 | 12/2002 | Peghini et al. |
| 2003/0055463 | A1 | 3/2003 | Gordon et al. |
| 2004/0006351 | A1 | 1/2004 | Gannoe et al. |
| 2004/0024386 | A1 | 2/2004 | Deem et al. |
| 2004/0059289 | A1 | 3/2004 | Garza Alvarez |
| 2004/0097986 | A1 | 5/2004 | Adams et al. |
| 2004/0116949 | A1 | 6/2004 | Ewers et al. |
| 2004/0122456 | A1 | 6/2004 | Saadat et al. |
| 2004/0122473 | A1 | 6/2004 | Ewers |
| 2004/0133147 | A1 | 7/2004 | Woo |
| 2005/0022827 | A1 | 2/2005 | Woo |
| 2005/0096638 | A1 | 5/2005 | Starkebaum |
| 2005/0267595 | A1 | 12/2005 | Chen et al. |
| 2006/0265042 | A1 | 11/2006 | Catanese, III et al. |
| 2006/0276871 | A1 | 12/2006 | Lamson et al. |

OTHER PUBLICATIONS

Cope, et al., "Percutaneous Transgastric Technique for Creating Gastroenteric Anastomoses in Swine", *Journal of Vascular and Interventional Radiology*, (2004) 15:177-181.

Cummings, et al., "Genetics and Pathophysiology of Human Obesity", *An Annual Review of Medicine*, (2003) 54:453-471/.

Johnston, et al., "The Magenstrasse and Mill Operation for Morbid Obesity", *Obesity Surgery*, (2003) 13:10-16.

Morino, et al. "Laparoscopic Adjustable Silicone Gastric Banding Versus Vertical Banded Gastroplasty in Morbidly Obese Patients" Analysis of Surgery. vol. 238, No. 6. 2003.

Roman, et al., "Intragastric Balloon for 'Non-Morbid' Obesity: A Retrospective Evaluation of Tolerance and Efficacy", *Obesity Surgery*, (2004) 14:539-544.

Sjostrom, et al., "Lifestyle, Diabeter, and Cardiovascular Risk Factors 10 Years After Bariatric Surgery", *New England Journal of Medicine*, (2004) 351(26):2683-2693.

Smith, et al., "Results and Complications of Gastric Partitioning: Four Year Follow-Up of 300 Morbidly Obese Patients", *The American Journal of Surgery*, (1983) 146:815-819.

Buchwald et. al. "Bariatric Surgery: A Systematic Review and Meta-analysis"; JAMA vol. 292, No. 14. pp. 1724-1737.

Camerini et al. "Thirteen Years of Follow-up in Patients with Adjustable Silicone Gastric Banding for Obesity; Weight Loss and Constant Rate of Late Specific Complications." Obesity Surgery, 14, pp. 1343-1348.

Sallet et. al. Brazilian Multicenter Study of the Intragastric Balloon; Obesity Surgery, 14, 991-998.

Smith, Lindsay B.; "Modification of the Gastric Partitioning Operation For Morbid Obesity". Am. J. Surgery 142, Dec. 1981.

\* cited by examiner

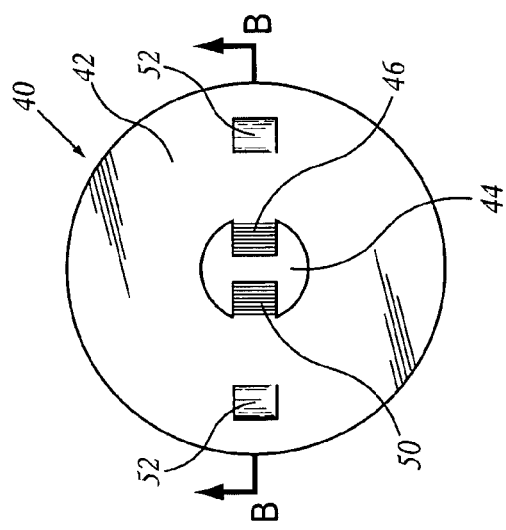
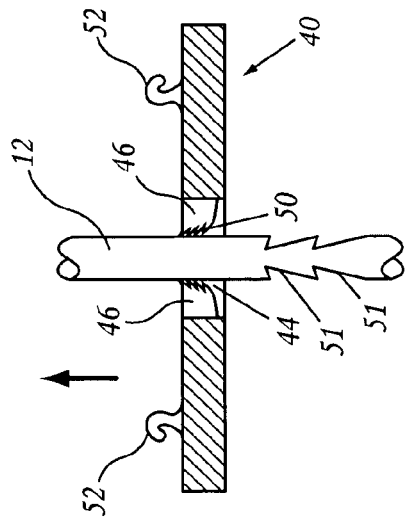
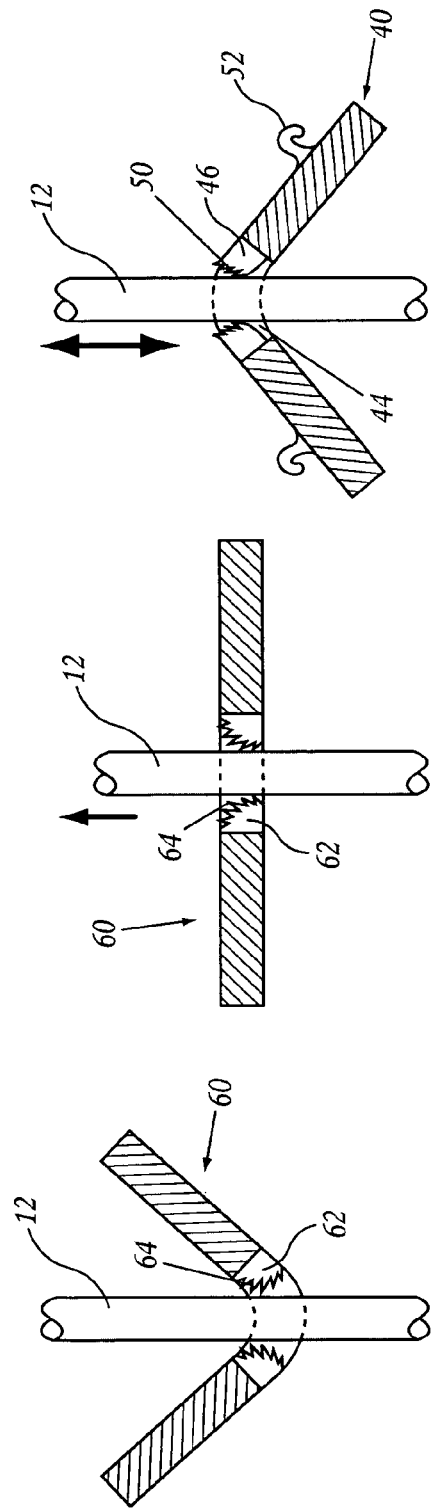

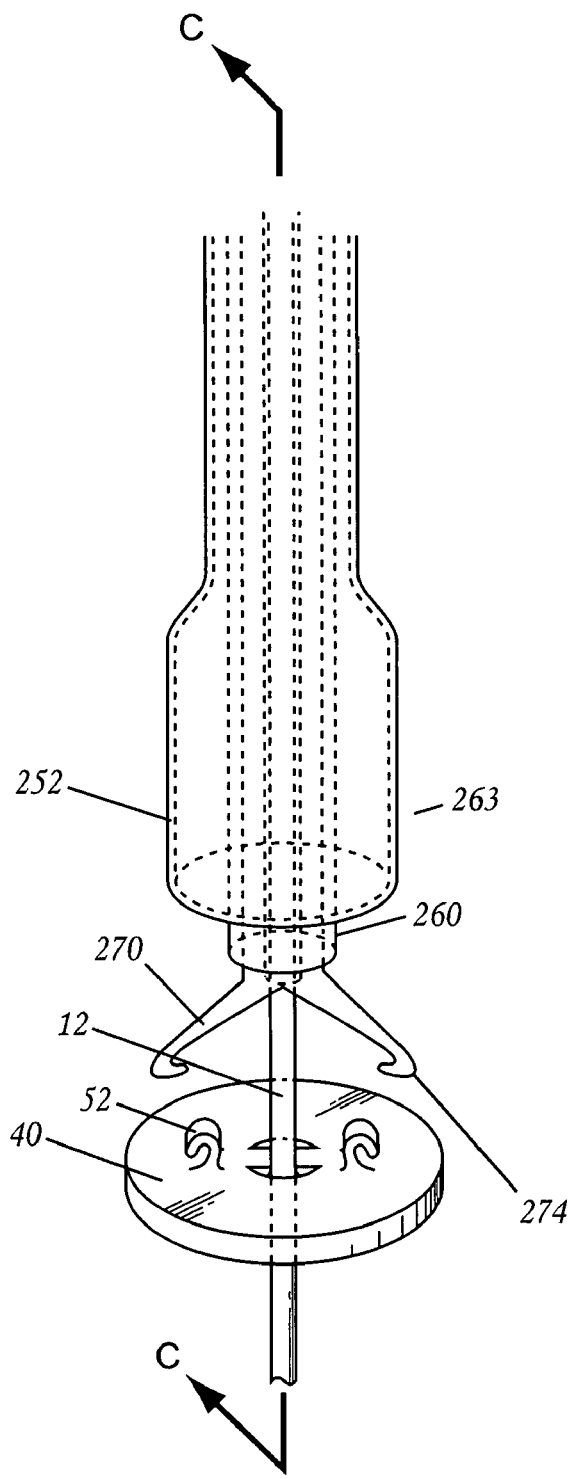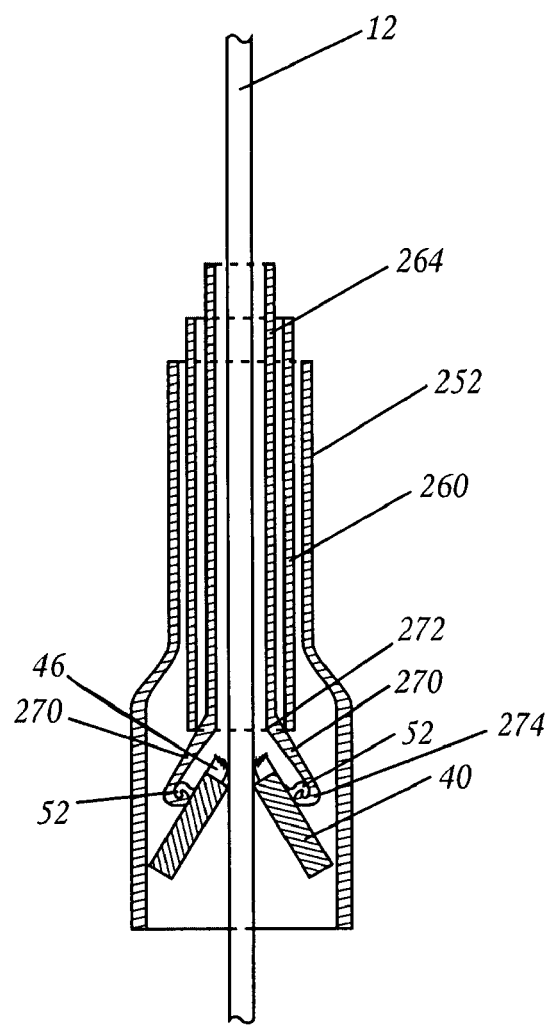
FIG. 5B
FIG. 5C

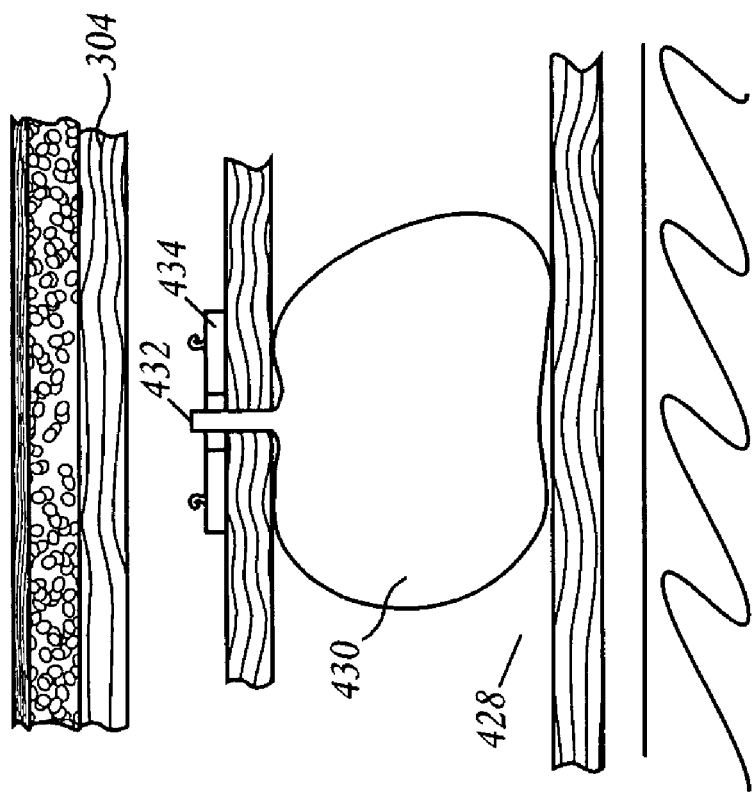
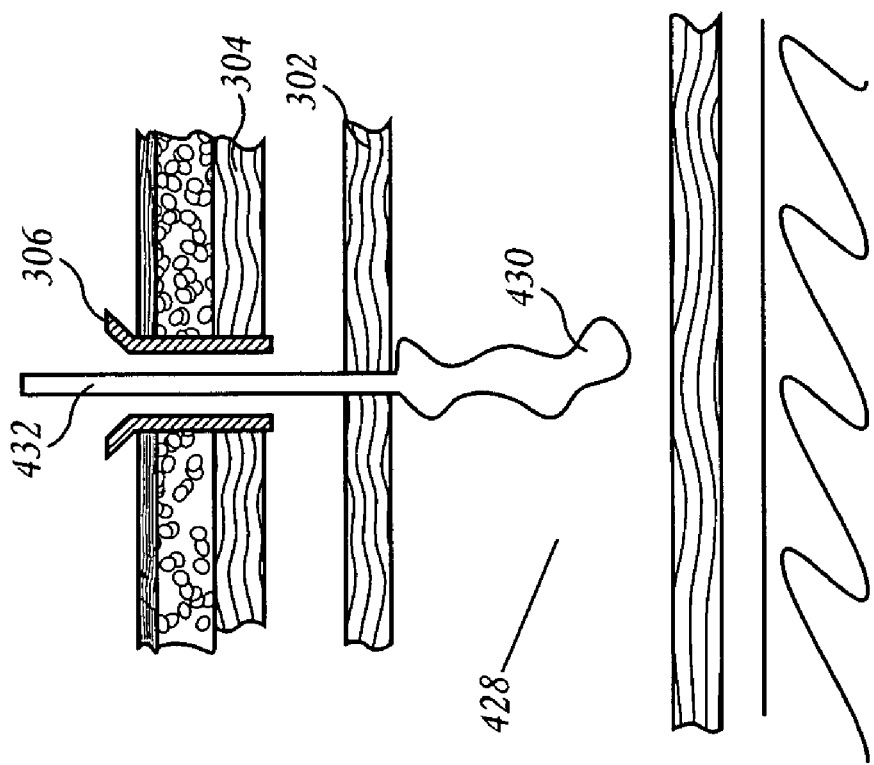
FIG. 10B
FIG. 10A

PERCUTANEOUS GASTROPLASTY

RELATED APPLICATIONS

The present application is a continutation-in-part of International Patent Application No. PCT/US05/09322, filed Mar. 19, 2005, designating the United States, entitled "DEVICE AND METHODS TO TREAT A PATENT," which is a continuation-in-part of U.S. Non-Provisional patent application Ser. No. 10/974,248 filed Oct. 27, 2004, now U.S. Pat. No. 7,255,675 entitled "DEVICES AND METHODS TO TREAT A PATIENT," which claims priority to U.S. Provisional Patent Application Ser. No. 60/556,004 filed Mar. 23, 2004 by Michael Gertner, M.D., entitled "BARIATRIC DEVICES AND IMPLANTATION METHODS," to U.S. Provisional Patent Application Ser. No. 60/584,219 filed Jul. 1, 2004 by Michael Gertner, M.D., entitled "DEVICES AND METHODS FOR PERCUTANEOUS GASTROPLASTY," to U.S. Provisional Patent Application Ser. No. 60/603,944 filed Aug. 23, 2004 by Michael Gertner, M.D., entitled "DEVICES AND METHODS TO TREAT MORBID OBESITY," all of which are herein incorporated by reference in their entirety.

BACKGROUND OF THE INVENTION

1. Field of the Invention

The present invention relates to methods and apparatus for implanting devices in the walls of organs or vessels, including devices to appose the walls of the stomach and blood vessels.

2. Description of the Related Art

Obesity is a public health problem of extreme national and international importance. There are an estimated 60 million obese adults and 2 million obese adolescents in the United States as of 2004. By some estimates, there are 1 billion obese individuals worldwide. Indeed, recent reports estimate that over there are over 60 million obese individuals in China, a 10-fold increase since 2000. Obesity affects the life quality and productivity of those effected and leads to long-term health related complications such as diabetes and heart disease. Some researchers estimate that if the obesity epidemic is not brought under control, it could quickly overwhelm societal resources.

To date, surgery is the only proven method for inducing substantial weight loss. The mechanism behind the success of surgery is, in many cases, not known because obesity is such a complex, multifactorial disease. Some researchers propose that surgery does no more than provide biofeedback for appetite retraining. Other researchers maintain that surgery alters the physiology of the patient such that satiety is induced earlier or fewer nutrients are absorbed. Nonetheless, all researchers agree that long-term weight loss is only possible by surgical means.

Over the past four decades, there have been numerous surgical procedures and devices developed to those who suffer from morbid obesity. In general, there are two physiologic components of all past and current procedures: malabsorption and mechanical restriction/volume reduction.

Many of the procedures performed in the past have proven to be impractical, dangerous, and/or detrimental to patient health and are now of historical importance only. One example of a failed procedure is the jejuno-ileo bypass in which a malabsorptive state was created through the bypass of a large portion of the intestine through the creation of a surgical anastomosis between the jejunum and the ileum. While patients initially lost a great deal of weight, liver failure or liver damage occurred in over one-third of the patients which necessitated reversal of the surgical procedure.

One of the first restrictive type surgical procedures was the so-called "stomach stapling" operation in which a row of horizontal staples was placed across the upper stomach and then several staples were removed from the staple line to create an opening, the "os" for a small amount of food, but not too much food. This procedure was mostly restrictive, leading to an early feeling of satiety. This surgery was abandoned because 70%-80% of patients had inadequate weight loss due to staple line dehiscence (i.e. the staples pulled through the stomach wall). A procedure to stabilize the staple line was performed by Smith et. al. (Lindsay B. Smith; Modification of the Gastric Partitioning Operation For Morbid Obesity. Am. J. Surgery 142, December 1981) in which the staple line was buttressed in the region where the staples were removed using teflon pledgets with sutures passing through the middle of the pledgets. The purpose of the pledgets was to buttress the suture and distribute the load across the suture to the pledget, thereby preventing the suture from pulling through the stomach and therefore stabilizing the os. The outcomes showed that the suture buttress was able to prevent the suture from tearing through the stomach wall.

The Roux-en-Y (The Roux) bypass operation has become the most commonly performed surgical procedure to treat the morbidly obese in the United States. It combines a small degree of malabsorption with a 90% reduction in the volume of the stomach. In the United States, 150,000 Roux procedures were performed in the year 2004. This number is expected to rise to 500,000 procedures by 2007. The procedure actually has been performed since the late 1970's but has evolved substantially over the past three decades into a relatively safe and effective procedure; indeed, the long-term data is very good. The advent of laparoscopic surgery and hence the laparoscopic Roux-en-Y bypass in combination with excellent follow-up results from the open procedure are reasons for the proliferation of the Roux procedure.

Despite the efficacy of the Roux procedure and the recent laparoscopic improvements, it remains a highly invasive procedure with substantial morbidity, including a 1-2% surgical mortality, a 20-30% incidence of pulmonary morbidity such as pneumonia, pulmonary embolism, etc., and a 1-4% chance of leak at the anastomotic site which can result in a spectrum of consequences ranging from an extended hospital stay to death. Furthermore, it is not a good option for adolescents in whom the long-term consequences of malabsorption are not known. In addition, many patients resist such an irreversible, life altering procedure.

The Roux procedure requires general anesthesia and muscle paralysis which, in the morbidly obese population, is not of small consequence. There is also a substantial rate of anastomotic stricture which results in severe lifestyle changes for patients. As an example, many patients are forced to vomit after meals. Furthermore, although minor when compared to previous malabsorptive (e.g. jejuno-ileal bypass) procedures, the malabsorption created by the Roux-en-Y can dramatically affect the quality of life of patients who undergo the procedure.

Recently, minimally invasive procedures and devices which create a feeling of early satiety have been introduced into the marketplace in an attempt to address some of the issues above. The LAP-BAND™ is a band which encircles the stomach at the region of the fundus-cardia junction; it is a restrictive procedure similar to stomach stapling. It requires general anesthesia, a pneumoperitoneum, muscle paralysis, and extensive dissection of the stomach at the level the gastroesophageal junction. Although less invasive than the Roux procedure and potentially reversible, the LAP-BAND™ is nonetheless quite invasive. It also does not reduce the volume of the stomach and some patients report a feeling of hunger much of the time. In addition, long-term follow-up reveals that the banding procedure results in many complications. In a recently published article (Camerini et.al. Thirteen Years of Follow-up in Patients with Adjustable Silicone Gastric Banding for Obesity: Weight Loss and Constant Rate of Late Specific Complications. Obesity Surgery, 14, 1343-1348), the authors reported a 60% prevalence of late band removal secondary to complications such as erosion, slippage of the band, infection, or lack of effectiveness. Nonetheless, the LAP-BAND™ as a procedure is becoming very popular across the world as it is perceived to be a less invasive and reversible procedure. The weight loss in long-term trials is considered adequate by some and inadequate by many; across the various studies, the average weight loss is approximately 40% of excess body weight (see below).

Other procedures which have been tried in the past and which offer varying degrees of weight loss include several variations of the original "gastroplasty" procedures. These procedures represent an evolution of the so-called "stomach stapling" procedure discussed above. These procedures were attempted prior to and concomitant with the evolution of the Roux-en-Y. They became popular (despite potentially offering less weight loss than the Roux) because of their substantially less invasive nature and possible reversibility.

One such example is called the vertical banded gastroplasty, or VBG, which again, created a restricting "os" for food. In the VBG, the border of the "os" is the lesser curvature of the stomach which is less apt to dilate than the fundus region of the stomach. Furthermore, the procedure completely excludes the fundus which is thought to easily dilate and in fact, is physiologically "programmed" to dilate during meals . . . so-called "receptive relaxation." One issue with the VBG is that, as practiced today, it is not reversible, nor is it adjustable, and it is difficult to perform laparoscopically. As in the horizontal gastroplasty, the VBG utilizes standard staplers which, as in the horizontal gastroplasty, are unreliable when applied to the stomach. In the case of the VBG, the row of staples runs parallel to the lesser curvature of the stomach.

A recent, prospective, randomized trial, compared the VBG to the adjustable banding procedure and found that the VBG was overwhelmingly superior to the banding procedure (Morino et. al. Laparoscopic Adjustable Silicone Gastric Banding Versus Vertical Banded Gastroplasty in Morbidly Obese Patients. Annals of Surgery. Vol. 238 (6) pps. 835-842). Twenty five percent of the patients in the banding group returned to the operating room whereas there were no returns to the operating room in the gastroplasty group. The degree of weight loss was close to 60% of excess body weight after three years in the gastroplasty group and closer to 40% of excess body weight in the banding group. Although in this study, the VBG was successfully performed laparoscopically, the laparoscopic VBG procedure is in fact, difficult to perform, because the procedure is not standardized and a "tool box" does not exist for the surgeon to carry out the procedure; furthermore, the procedure is not a reversible one and relies on the inherently unreliable stapler systems. A recent meta-analysis and systematic review (Buchwald et. al. Bariatric Surgery: A Systematic Review and Meta-analysis; JAMA vol. 292, no 14. pps 1724-1737) indicated that vertical gastroplasty (avg. excess weight loss of 68.2%) is superior to adjustable banding (avg excess weight loss of 47.5%) and gastric bypass (avg excess weight loss of 61.6%).

The Magenstrasse and Mill (M&M) procedure is an evolving gastroplasty technique wherein the greater curvature of the stomach is separated (stapled and cut) from the path of food, leaving a tube of stomach, the Magenstrasse, or "street of the stomach," which is comprised of the lesser curvature. This procedure is similar to the VBG except that the longitudinal staple line of the stomach extends further along the lesser curvature and into the antrum. The theory behind leaving the antral "mill" is that it will continue to serve its normal function of mixing, grinding, retropulsion, and well-orchestrated expulsion of chyme into the duodenum. An authoritative study on the operation is incorporated herein by reference (Johnston et. al. The Magenstrasse and Mill Operation for Morbid Obesity; Obesity Surgery 13, 10-16).

In summary, the vertical gastroplasty procedure appears to be superior to the banding procedure. However, the vertical gastroplasty procedure is not easily performed laparoscopically and furthermore, it is not reversible. Therefore, a need exists to standardize the vertical banded gastroplasty and create a safer procedure which is also easy to perform, is durable and is reversible.

The intragastric balloon is not a new concept. The intragastric balloon is meant to displace volume within the stomach such that a smaller volume of food leads to an earlier feeling of satiety. Currently, intragastric balloons on the market are not fixed to the stomach. As a consequence, the intragastric balloons lead to complications such as obstruction and mucosal erosion. As a consequence, the balloons are removed after a maximum of six months. In a prospective, non-randomized, unblinded study (Sallet et. al. Brazilian Multicenter Study of the Intragastric Balloon; Obesity Surgery, 14, 991-998), the average excess weight loss was 48.3% after 1 year. However, the incidence of nausea and vomiting was 40% and epigastric pain was 20%; balloon impaction occurred in 0.6% of patients. A balloon which is fixed to the wall of the stomach could potentially improve the intragastric balloon device and allow longer-term implantation.

More recently, there has been an effort to develop even less invasive devices and procedures which do not involve incisions at all. For the most part, these procedures are performed from within the stomach with an endoscope and by a phyisician with a high degree of endoscopic skill. For example, U.S. Pat. No. 6,558,400 describes methods and devices to create partitions in the stomach. Anchors or staplers applied through an endoscope from within the stomach are used to accomplish the partitions. Similarly, U.S. Patent Application Publication No. 2004/0122456 describes another set of methods and devices to reduce the volume of the stomach. Expandable anchors are deployed both on the anterior and posterior wall of the stomach using an endoscope. Flexible sutures are brought out of the patient's mouth and the sutures are crimped together within the stomach in order to bring the walls of the stomach closer together. Patent application WO2004/004542 describes a device which is advanced through an endoscope and grasps or applies suction to a fold of mucosa to apply anchors through the mucosal and serosal layers of the stomach.

Endoscopic procedures to manipulate the stomach are time consuming because of the technical difficulty of the endoscopy; they also require a large endoscope through which many instruments need to be placed for these complex procedures. Due to the large size of the endoscope, patients typically will require general anesthesia, which limits the "non-invasive" aspects of the procedure. Furthermore, the procedures require advanced endoscopic skill which would need to be acquired by most endoscopic practitioners. Such skill adaptation can take a significant amount of time, which will limit adoption of the procedure by the physician community. A further issue is that there is a limitation on the size of the anchors and devices which can be placed because the endoscope has a maximum size.

Percutaneous Endoscopic Gastrostomy (PEG) refers to a procedure in which a gastrocutaneous tract is created using a percutaneous procedure (see below for definition). A recent update of the procedure can be found on the Society of American Gastrointestinal Endoscopic Surgeons (SAGES) website, and is incorporated herein by reference. Briefly, the procedure involves insufflation of the stomach with and under visualization with an endoscope. A small incision is made in the skin and a needle is advanced into the stomach (the stomach sits just under the abdominal wall when insufflated) under endoscopic visualization. A feeding tube is then placed over the needle to create a gastrocutaneous tract with the feeding tube inside the tract. The feeding tube is secured with an external bolster to creates a tubular tract from outside the patient through the skin of the abdominal wall and residing inside the stomach. Over the ensuing weeks, a permanent tract evolves between the stomach mucosa and epithelium of the skin, after which, the bolster can be removed without consequence. When the feeding tube is to be removed, the gastrocutaneous tract will close on its own as food will preferentially be delivered antegrade (the path of least resistance) to the duodenum, thereby allowing the tract to heal.

SUMMARY OF THE INVENTION

In one embodiment, the current invention expands the scope of percutaneous gastrostomy in order to reduce the volume of the stomach, implant devices, and otherwise manipulate the stomach. Such procedures can be easily adopted by the surgical community.

In one embodiment, a method for implanting an organ traversing device in a patient is disclosed. A first surgical instrument is placed adjacent to a second exterior surface of an organ. A first end of a second surgical instrument is passed through a patient's skin, through a first exterior surface of the organ, through the interior of the organ, and thence through a second exterior surface of the organ, so that the surgical instrument traverses the organ. The first surgical instrument then contacts the second surgical instrument and a first anchor is deployed from the first surgical instrument wherein the first anchor is located adjacent to the second exterior surface of the organ. Subsequently, a second anchor is deployed within the patient. At least one connector is provided wherein the at least one connector contacts the first anchor. The first and second anchors are stabilized by engaging the at least one connector with the first and second anchors. The anterior and posterior anchors can further be urged toward each other such that a tensile stress then exists in the at least one connector. The second anchor can contact the second exterior surface of an organ of a patient or it can contact one of the abdominal wall layers. The organ can be the stomach of a patient and the skin can overlie the patient's stomach. The first exterior surface can be the anterior wall of the stomach and the second exterior surface of the organ can be the posterior wall of the stomach.

The anterior and posterior walls of the stomach can be urged closer together by shortening the length of the at least one connector. The first or second surgical instrument can be inserted into the patient's abdomen by directly penetrating the patient's skin and abdominal wall or by passing the surgical instrument through a laparoscopic port or by passing the surgical instrument through an incision in the patient's skin and abdominal wall.

In another embodiment, a method for treating a patient involves passing a first anchor through the skin of a patient and positioning the first anchor adjacent to the posterior wall of the stomach and then passing at least one connector through the patient's skin and thence through the patient's anterior and posterior stomach walls to contact the first anchor and the at least one connector, then passing a second anchor through the skin of a patient's abdominal wall. The first and second anchors are linked by means of the at least one connector. The first and second anchors are urged toward each other and fixed to the connector either reversibly or irreversibly, thereby fixing the anterior and posterior walls of the stomach in the urged position with said first and second anchors.

In another embodiment, the second anchor is deployed within the peritoneal cavity and in yet another embodiment, the second anchor is deployed between the abdominal skin and the outermost peritoneum of the abdominal cavity. In one embodiment, the first anchor passes through the patient's abdominal skin while the first anchor is in a reduced profile configuration; subsequently the first anchor is expanded to reside in a deployed configuration.

The reduced profile configuration of the first anchor in some embodiments is substantially folded, and/or compressed, and/or uninflated, and said deployed configuration is substantially unfolded and/or uncompressed and/or inflated.

The reduced profile configuration of the second anchor in some embodiments is substantially folded, and/or compressed, and/or uninflated, and said deployed configuration is substantially unfolded and/or uncompressed and/or inflated.

In some embodiments, the anchor implantation method is repeated for additional anchors. In some embodiments, the mucosa of said anterior and posterior walls of the stomach do not contact one another (or when they do contact one another, food can continue to pass through even though at a slower rate) when said first and said second anchors are fixed in their urged positions. In other embodiments, the mucosa of said anterior and posterior walls contact one another tightly (prevent food from passing) when said first anchor and said second anchor are fixed in their urged positions. In some embodiments, an electrical signal is delivered to the anterior stomach wall through the second anchor. In some embodiments, an electrical signal is delivered to the posterior stomach wall through a first anchor. In some or all embodiments, an endoscope is not used to grasp the stomach.

In another embodiment, a method for fastening or otherwise applying or implanting a therapeutic device to a wall of a gastrointestinal organ is described. The therapy device is passed through a patient's abdominal skin and into or close to the serosa of a gastrointestinal organ. In some embodiments, the therapy device is in an undeployed configuration and is subsequently deployed in the serosa or muscular layers of the gastrointestinal organ. In some embodiments, a connector is also provided for attachment to the therapy device. In some embodiments, an anchor is further placed through the abdominal skin of a patient while the anchor is in an undeployed configuration. The anchor is subsequently deployed in the serosal or muscular layers of the organ or in the abdominal wall; in this embodiment, pneumoperitoneum is not necessary nor is penetration of the mucosal layer of the organ. In some embodiments, the anchor is connected to the therapy device by means of the connector. The method of this embodiment can also be applied to non-permanent (non-implantable) devices; for example, a temporary or permanent therapeutic energy source can also be applied to the gastrointestinal organ without a generalized pneumoperitoneum. Examples of temporary energy sources in this embodiment include but are not limited to radiofrequency generators, microwave generators, laser generators, or ultrasound generators.

In one embodiment, a method of treating a patient is described in which a surgical device having a reversibly engaged first anchor is positioned near an organ or organ-organ connection or anastomosis of a patient. An elongate member, which has a proximal end, a distal end, and a circumferential wall sized to receive at least one connector, is positioned or formed in a patient. The distal end of the connector is then engaged by the first anchor after the distal end of the connector is advanced through the lumen of the elongate member, through a first portion of the organ and thence through a second portion of the organ. The first anchor is then released from the surgical device such that the first anchor remains engaged with the connector. Subsequently, a second anchor is advanced over the connector while tracking along the connector. The first and second anchors are then urged together, the second anchor is released such that it engages the connector. The connector is then cut such that its length defines the distance between the first and second anchors.

The organ, or organ-organ anastomosis of treatment can be one of: the stomach, lung, colon, intestine, liver, spleen, a vein, an artery, the small intestine, a gastroenterostomy, a gastrojejunostomy, a colo-colostomy, or a colo-enterostomy.

In another embodiment, a method for creating a feeling of fullness in a patient involves passing a volume displacing device through the skin of a patient and into the space between the abdominal musculature and the anterior wall of the stomach. The volume displacing device has an expandable portion and a connector portion. The expandable portion is then expanded. The volume displacing device is then secured to the abdominal wall by tracking a anchor over the connector portion of the volume displacing device and deploying the anchor. When the anchor is deployed on the connector, the anchor is prevented from moving further along the connector. In some embodiments, the volume expandable portion of the volume displacing device is fixed to the serosa of the stomach and does not penetrate the mucosal layer. In some embodiments, the connector is cut at the level of the anchor.

In some embodiments, the anchor connector system or systems in any of the embodiments of the invention is adjusted from within the stomach after the fastening system is placed and after the connector is cut. Adjustability of the transgastric fastening system is advantageous over the prior art.

BRIEF DESCRIPTION OF THE DRAWINGS

FIGS. 2A and 2B are a perspective view and top view of one embodiment of an anterior anchor, respectively.

FIGS. 2C and 2D are side sectional views of the embodiment of the anterior anchor of FIGS. 2A and 2B, taken along the line B-B in FIG. 2B, in its deployed and reduced profile configuration, respectively.

FIGS. 2E and 2F are side sectional views of another embodiment of an anterior anchor, taken along the same line as FIGS. 2C and 2D, in its deployed and reduced profile configuration, respectively.

FIG. 5B is a perspective view of the distal end of the anchor implantation instrument of FIG. 5A and an anterior anchor and connector.

FIG. 5C is a side sectional view of the distal end of the anchor implantation instrument of FIGS. 5A and 5B, taken along line C-C in FIG. 5B, with the anterior anchor in its reduced profile configuration.

FIG. 10A illustrates one embodiment of a method for deploying a volume displacing device in the stomach. Shown is a side sectional view of a patient's abdomen after an uninflated balloon anchor has been inserted inside the patient's stomach with a connector passing out of the stomach, through the anterior stomach wall, and through a laparoscopic port.

FIG. 10B illustrates one embodiment of a method for deploying a volume displacing device in the stomach. Shown is a side sectional view of a patient's abdomen with the balloon anchor in its deployed position, held in place by an anterior anchor and connector.

DETAILED DESCRIPTION OF THE PREFERRED EMBODIMENT

Anatomy of the Stomach

Figure 1A:
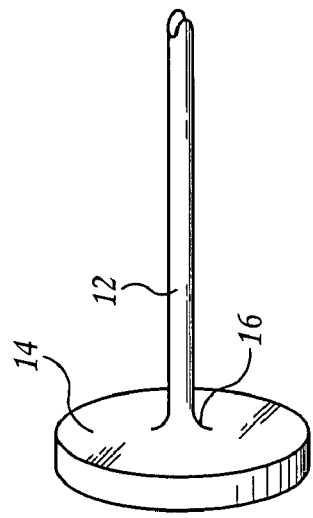
FIGS. 1A-1E are perspective views of embodiments of the posterior anchor and connector.

The region behind the stomach is referred to as the lesser peritoneal sac. It is a potential space between the retroperitoneum and the posterior wall of the stomach. To the left of the midline, the posterior wall of the stomach is generally free from the peritoneal surface of the retroperitoneum. To the right of the midline, the posterior wall of the stomach is more adherent to the retroperitoneum although the adherence is generally loose and the adhesions can be broken up rather easily with gentle dissection.

The stomach is comprised of several layers. The inner layer is the mucosa. The next layer is the submucosa followed by the outer muscular layers. Surrounding the muscular layers is the serosal layer. This layer is important with regard to implants and healing because it is the adhesive layer of the stomach; that is, it is the layer which, when breached, heals with scar tissue formation. Implants adhering to this layer are less likely to migrate into the stomach. Reference to "stomach wall" or "wall of the stomach" as used herein include the entire thickness of the stomach, including the mucosa, submucosa, muscular layers, and serosa. The "anterior wall of the stomach" is the portion of the stomach closest to the muscular abdominal wall and the "posterior wall of the stomach" is the part of the stomach closest to the retroperitoneum.

"Transgastric fastening assembly" or "fastening system" refers to a permanent or semi-permanent implant and comprises at least one posterior anchor, at least one anterior anchor, and a connector to couple the posterior and anterior anchors. The "connector" can refer to any means of connection including but not limited to a material connection, an electromagnetic connection, or a chemical connection. As used herein, a "connector" is a coupler or linker used to materially connect the anterior and posterior anchors. As used herein, the "posterior anchor" is the anchor in a preferred embodiment which is adjacent to the posterior wall of the stomach when deployed. The "anterior anchor" is the anchor in a preferred embodiment which is approximated to the anterior wall of the stomach when deployed.

As used herein and when referring to portions of a surgical instrument, "proximal" refers to the end of the instrument which is closest to the surgeon when the instrument is used for its intended purpose, and "distal" refers to the end of the instrument which is closest to the patient when the instrument is used for its intended purpose. When used to refer to the gastrointestinal tract, "proximal" is toward the mouth and "distal" is toward the anus.

"Laparoscopic procedure" broadly refers to procedures which require pneumoperitoneum and general anesthesia. "Percutaneous procedure" broadly refers to surgeries which do not require general anesthesia or pneumoperitoneum. These broad terms are mutually exclusive for the purposes of the ensuing invention because the respective procedures require different levels of patient preparation and peri-operative treatments. In some descriptions, the terminology "percutaneous means" is used which generically refers to placing a surgical instrument through the skin of a patient and using the surgical instrument to accomplish a surgical task; in this more generic case, "percutaneous means" can be used with or without laparoscopy. Similarly, "laparoscopic means" generically refers to procedures performed under the guidance of an internal camera; in this more generic sense, laparoscopy can be used with or without percutaneous methodology though in most cases percutaneous methodology is preferred.

Structures

Transgastric Fastening Assembly

Figure 1B:
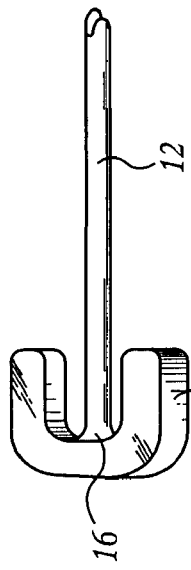

Referring to FIGS. 1A and 1B, one embodiment of the posterior anchor 14 and connector 12 are shown in a deployed configuration (FIG. 1A), and reduced profile configuration (FIG. 1B). The connector 12 is preferably made of a flexible, biocompatible polymer, but it can be made from various kinds of suitable biocompatible materials known to those of skill in the art including metals, such as titanium and platinum, metal alloys, such as stainless steel, nickel-titanium, and cobalt-chromium, man-made polymers, such as polyurethane, silicone elastomers, polyglycolic acid, polylactic acid, poly (ε-caprolactone), polyvinylidene fluoride (PVDF), PTFE, FEP, polypropylene, or natural fibers such as silk; bioartificial materials include allogenic and xenogenic collagen based products. These materials can be used singly or in combination. For example, one portion of the connector may be bioabsorbable and another portion of the connector may be permanent. The connector 12 can vary in thickness, shape, and rigidity. For example, in the embodiment shown in FIG. 1A, the connector 12 is substantially rod-shaped, with a circular cross-section, and is flexible. Those of skill in the art will recognize that the cross-section of the connector can be any of a number of shapes, such as square, hexagonal, oval, etc. In other embodiments, the connector 12 is thin and flexible, such as a surgical suture, and in still others it is rigid. The connector can have a thickness ranging from 100 microns (e.g. suture) to several millimeters depending on the application. Although a single connector is depicted as being attached to the posterior anchor, those skilled in the art will recognize that more than one, or several connectors can be connected to the anchor at different points on the anchor or as a combination attached to one point on the anchor (e.g. a bundle).

Figure 1C:
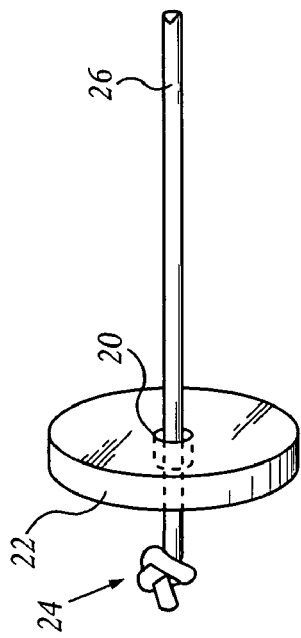

In a preferred embodiment, the posterior anchor 14 is made from a biocompatible, radio-opaque or magneto-opaque semi-rigid polymer; it can also be made from various kinds of suitable materials known to those of skill in the art including metals, metal alloys, plastics, natural materials or combinations thereof as discussed above in relation to the connector 12. In some embodiments, the anchor is made from a conductive material and in other embodiments, the anchor is made from a combination of conducting, non-conducting, and/or semi-conducting materials. The posterior anchor 14 can be solid, or alternatively, can be porous, mesh-like, lattice-like, or umbrella-like. In some embodiments, the anchor contains a potential space on the inside which can be expanded by a fluid (e.g. gas or liquid). In a preferred embodiment, the posterior anchor is porous or has a porous mesh attached to it to encourage fibrous ingrowth such that it becomes permanently attached to the stomach or intestinal wall. Coatings can be added to the anchor to encourage tissue ingrowth; of course, such coatings do not limit the ability for the interior of the anchor to be a potential space for expansion by a fluid. In other embodiments, the posterior anchor is solid and/or treated to discourage tissue ingrowth (e.g. with a silicone coating). In other embodiments, the posterior anchor has a xenograft or allograft material attached to the anchor. In a preferred embodiment, the posterior anchor 14 is disc-shaped, but those of skill in the art will recognize that other embodiments are possible, such as those shown in FIGS. 1C and 1D, or disclosed in U.S. Patent Application Publication No. 2004/0122456 which is herein incorporated by reference; note particularly the description of anchor structures. The posterior anchor, in other embodiments, can be rectangular or diamond shaped. The posterior anchor can also be bioabsorbable in whole or in part in some embodiments. The largest dimension of the posterior anchor can range from about 5 mm to about 10 cm depending on the application and the manner in which it is implanted (see below). In the case where the posterior anchor is a disc shape, the diameter is considered the largest dimension.

In the embodiment shown in FIGS. 1A and 1B, the connector 12 is fastened to the posterior anchor 14 at an attachment point 16 which is preferably a permanent, e.g. welded or molded, connection. Such a weld or connection can comprise, for example, a thermoformed polymer, a metallic weld, or a molded or other integral structure. In a preferred embodiment, a biocompatible thermoformed polymer is used because of its flexibility and ability to yield to the continuous motion of the stomach. More preferably, the connector and posterior anchor are produced as a single, continuous structure (e.g. through an injection molding process).

Other suitable means of fastening the connector to the posterior anchor are also contemplated and do not necessarily result in a connector and posterior anchor becoming permanently attached. For example, in one embodiment shown in FIG. 1C, one end of the connector is passed through a hole 20 near the center of the posterior anchor 22, and a stop 24, such as a knot or enlarged molded region, is formed on the end of the connector to prevent its passage back through the hole in the posterior anchor. In this embodiment, the posterior anchor 22 can be free to move along the length of the connector 26, but is prevented from being removed from one end of the connector by the stop 24.

In the embodiment shown in FIGS. 1A and 1B, the posterior anchor 14 preferably has a deployed configuration (FIG. 1A), and reduced profile configuration (FIG. 1B). The posterior anchor 14 can be deformed to a folded configuration wherein its profile is reduced to facilitate insertion of the anchor through the walls of the stomach or other tissue as described in more detail below. In one embodiment, the posterior anchor 14 is made of a semi-flexible material having shape memory, so that once the anchor is deployed within the patient, it will return to its original shape shown in FIG. 1A, preventing it from being easily pulled back through the tissue. Preferably, the posterior anchor is inflatable in place of, or in addition to, having shape memory, which allows for a much larger deployed profile relative to its undeployed profile (see below). In some embodiments, the posterior anchor contains an intrinsic magnetic, ferromagnetic, or paramagnetic material.

Figure 1D:
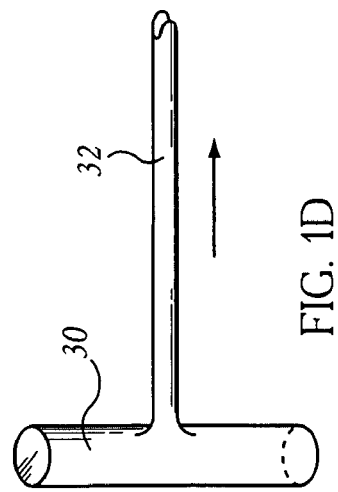
Figure 1E:
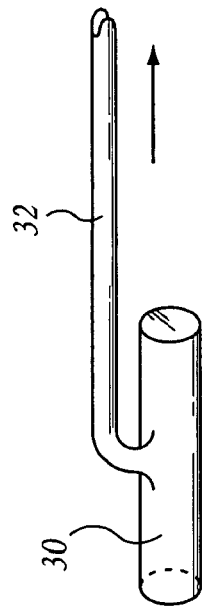

FIGS. 1D and 1E show an alternative embodiment of the posterior anchor 30 and connector 32 in a deployed configuration (FIG. 1D), and a reduced profile configuration (FIG. 1E). In this embodiment, the posterior anchor 30 is elongated, having major and minor dimensions, and preferably having a rod or bar shape. By aligning the connector 32 substantially parallel to the posterior anchor 30, its profile is reduced to facilitate insertion of the anchor through the walls of the stomach or other tissue. When the anchor leaves its surrounding sheath (see below), tension on the connector 32 in the direction of the arrow in FIG. 1E will urge the posterior anchor 30 into a substantially perpendicular orientation relative to the connector 32, as shown in FIG. 1D, preventing it from easily being pulled back through the tissue. The connection between the posterior anchor 30 and the connector 32 can be hinged. Alternatively, the connector 32 can be made of a semi-rigid material which is permanently connected or welded to the posterior anchor 30. If the connector is deformed to a bent position, shown in FIG. 1E, it will return to its original straight shape shown in FIG. 1D once the anchor is deployed within the patient, preventing the posterior anchor from easily being pulled back through the tissue. This anchor 30 can be inflatable as well, which allows for a much larger deployed profile relative to its undeployed profile.

Figure 1G:
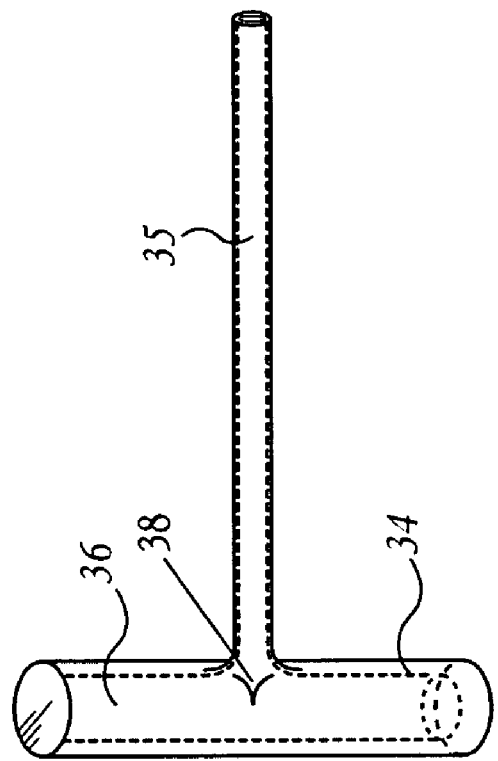
FIGS. 1F and 1G are side views of an inflatable embodiment of posterior anchor and connector.
Figure 1F:
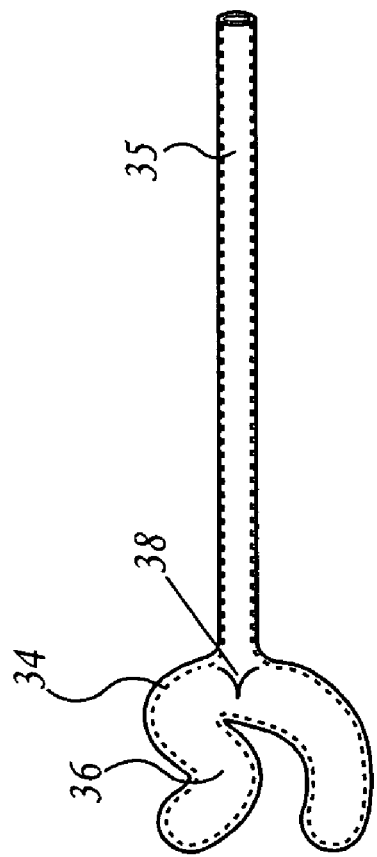

In a preferred embodiment, shown in FIGS. 1F and 1G, the posterior anchor is inflatable. The anchor has an inflatable disc-shaped body 34 which is readily deformable when in its reduced profile (i.e., uninflated) configuration as shown in FIG. 1F. In the preferred embodiment, the posterior anchor body 34 is disc-shaped, but those of skill in the art will recognize that other embodiments are possible, such as those shown in FIGS. 1C and 1D, or in which the inflatable anchors are square shaped, rectangular, or amorphous, or have a shape disclosed in U.S. Patent Application Publication No. 2004/0122456 which is herein incorporated by reference; note particularly the description of anchor structures. The body can be inflated with a substance delivered through a hollow connector 35. When the interior space 36 of the anchor body is inflated, the anchor assumes its deployed configuration shown in FIG. 1G. Once the body is inflated, it can become substantially less compliant yet remain soft and pliable.

The inflatable posterior anchor can have a valve 38 located between the anchor body 34 and the connector 35. Alternatively, the valve is located in the portion of the connector located outside the patient, the valve (e.g. stopcock type valve) being controlled by the operator until the anterior anchor is placed (see below). In this alternative embodiment, the filling substance is trapped in the posterior anchor after the anterior anchor is deployed and the connector is cut and sealed, preferably flush with the anterior anchor (see below). The filling substance can be a gas, liquid, or material which changes phase with time (i.e. it may harden, cure, polymerize, or become a gel with time). Preferably, the surface of the posterior anchor adjacent to the posterior wall of the stomach has a mesh fixed to it to encourage tissue ingrowth. In some embodiments, part, or all of the anchor material is comprised of a biodegradable material.

Figure 1J:
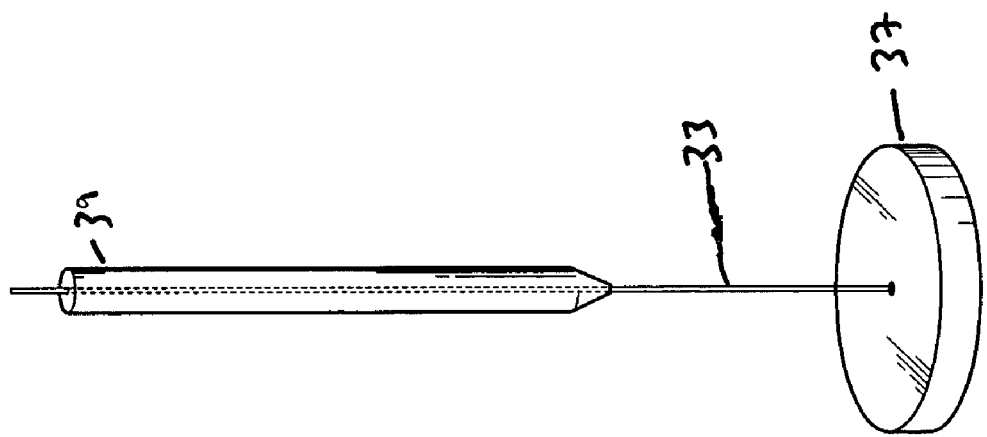
FIGS. 1H, 1I, and 1J are views of suture-connector—posterior anchor combinations in which the connector is separable from the posterior anchor.
Figure 1I:
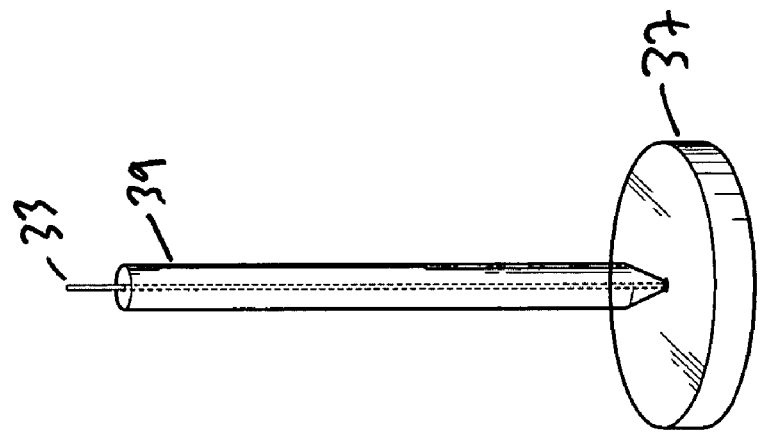
Figure 1H:
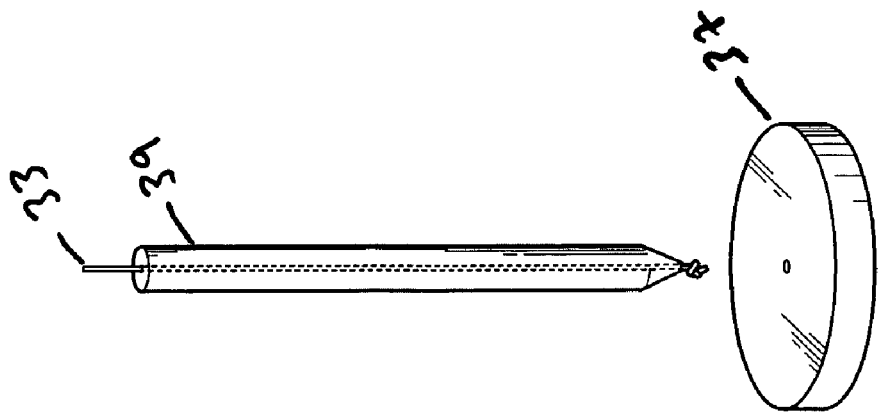

FIG. 1H depicts another embodiment of the current invention. The posterior anchor 37 and the connector 39 are separable in this embodiment. A second connector 33 is disposed within the first connector 39. The second connector can be one or more sutures. This fastening assembly would be used in a laparoscopic procedure where the connector 39 would be placed through an organ before engaging the posterior anchor 37. In some embodiments, the posterior anchor can be as large as the width of the organ (e.g. 8-10 cm in the case when the organ is the stomach). In some embodiments, the anchor 37 can be as small as 5 mm or 1 cm. The anchor 37 can also be adapted to accommodate several connectors rather than one connector at a time. The first connector 39 is adapted to engage the posterior anchor 37 after passing through tissue (e.g. the stomach). In one embodiment, the first connector has an inner diameter with a second connector (e.g. a suture) traveling through its lumen. After contact between the outer connector 39 and the posterior anchor 37, the outer connector 39 is removed, leaving the inner connector 33 (e.g. the suture) attached to the posterior anchor 37 (FIG. 1J). The connection of the suture to the posterior anchor is accomplished by any mechanical means well known to those skilled in the art.

Figure 1K:
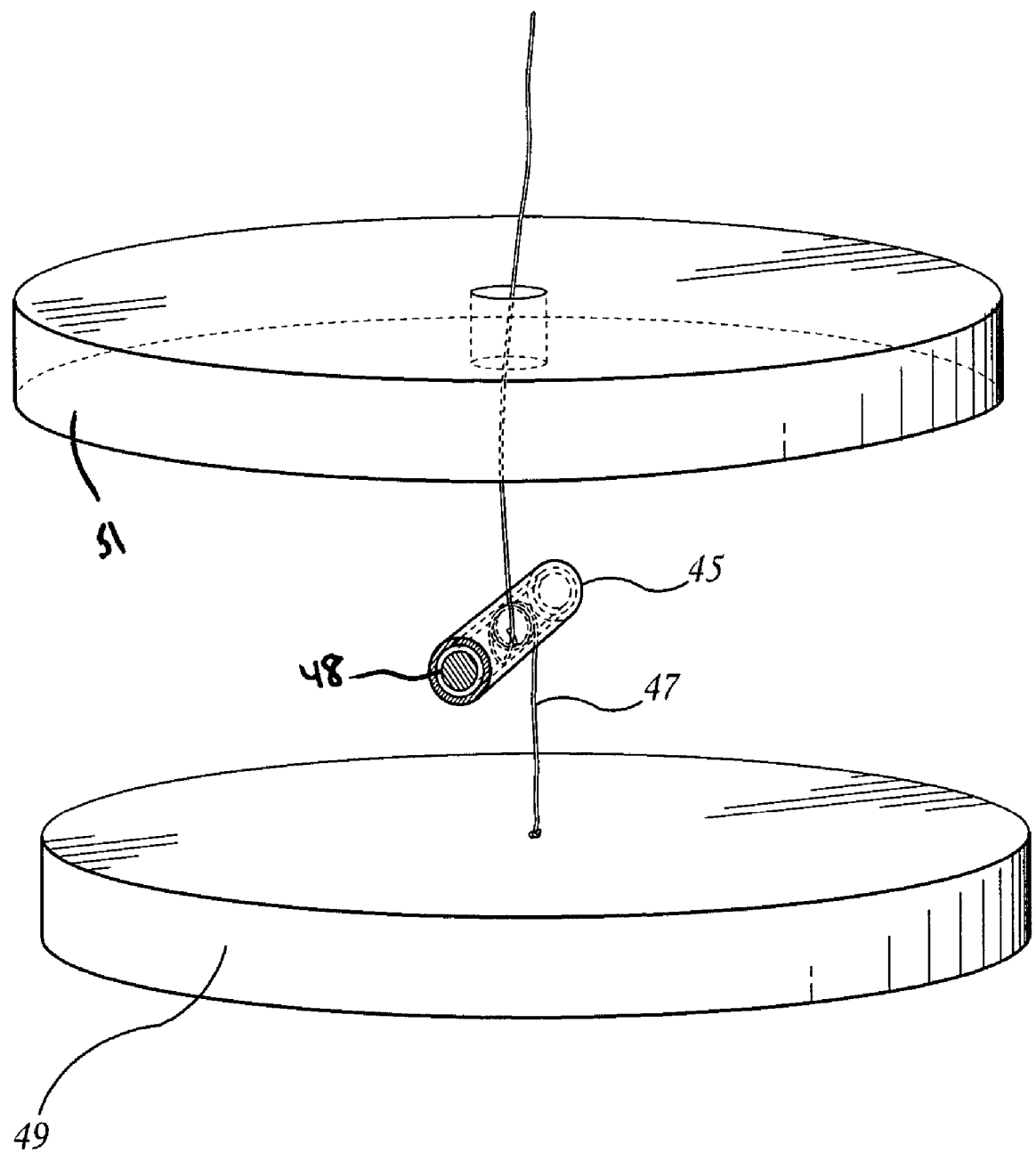
FIG. 1K is a view of a connector-anchor combination in which the length between two anchors is adjustable.

FIG. 1K depicts another embodiment of the current invention in which the connector 47 in this embodiment is configured so that its length is adjustable. In this embodiment, the connector is split (e.g. two sutures are used). The housing 45 is attached to one half of the connector 47 and this half of the connector is attached to the posterior anchor 49. Within housing 45, the connector 47 can be shortened (and the tension between thehh two anchors increased) by turning inner cylinder 48 which changes the distance (and the tension on the connector) between the two anchors 49,51. Such adjustment can be done with an endoscope and can be done after (days, months, years) implantation of the fastening system within an organ such as the stomach.

Although FIGS. 1a-k depict a single connector contacting the posterior anchor, those skilled in the art will recognize that more than one connector can be used to contact the posterior connector. The more than one connector can be placed in any arrangement along the posterior anchor (e.g. in a row, in a pattern along the perimeter, or concentrated in the center). The more than one connector can be bundled and attached in one place on a second anchor or in multiple point on a second anchor.

Figure 2A:
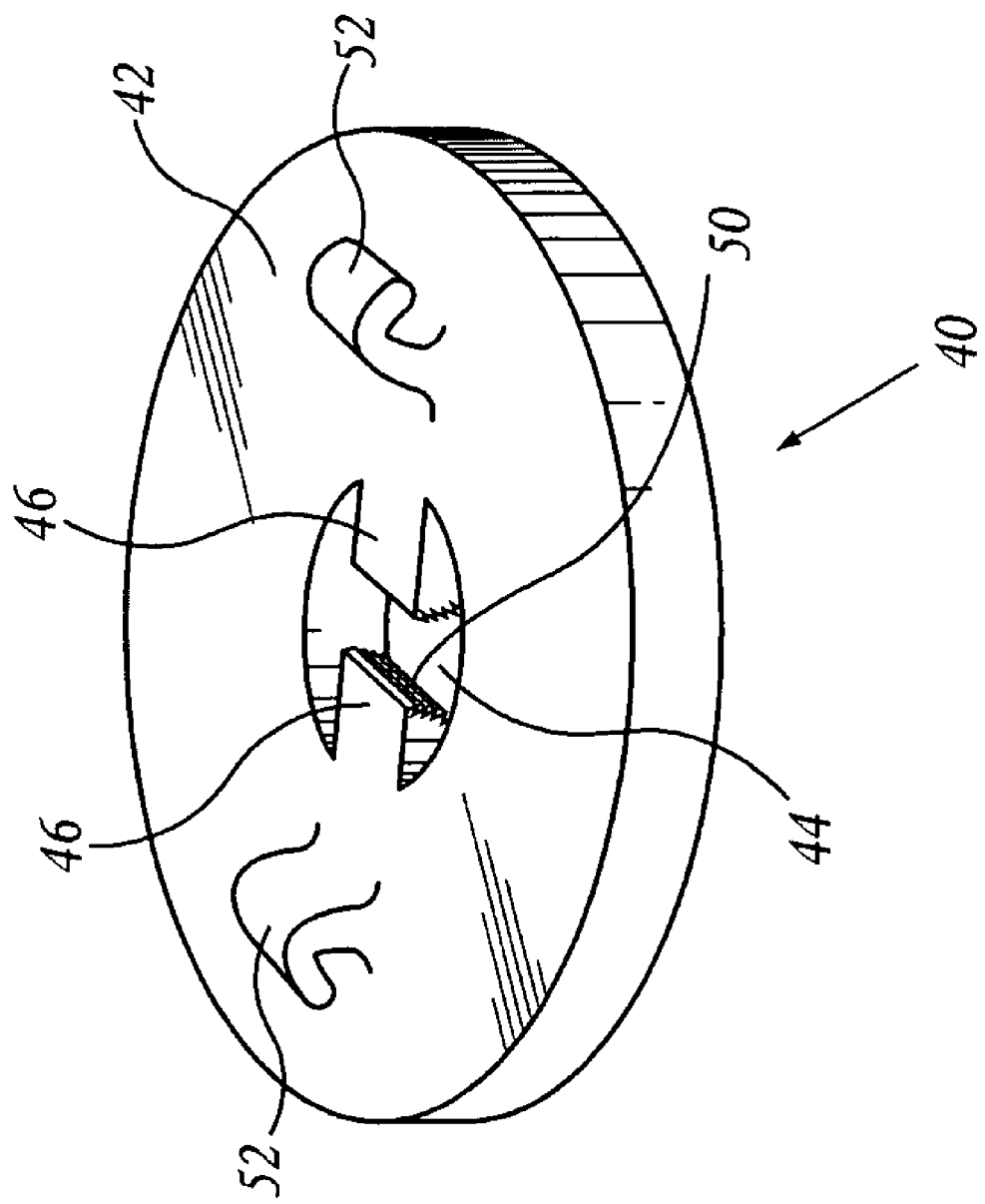

FIGS. 2A (perspective view) and 2B (plan view) show an embodiment of the anterior anchor 40. The anterior anchor has a disc-shaped body 42 with a hole or other passageway 44 substantially in the middle of the body. Although the hole is shown in the center of the anchor, those skilled in the art will recognize that the hole can be placed anywhere along the face of the anterior anchor and/or more than one hole can be created in the anchor. Two gripping elements 46 project into the center of the hole or other passageway. With respect to the gripping elements, there can be as few as one or more than two. The gripping elements can circumscribe the entire opening or they can be discrete components 46. The gripping elements can be macroscopic as shown in FIG. 2A or they can be microscopic like sandpaper (not shown). The gripping elements may have teeth 50 angled toward the top surface of the anchor. Optionally, two hooks 52, or other graspable recesses, appendages, or structures, are located on the top surface of the anterior anchor. Hooks 52 allow for attachment of a surgical instrument during deployment of the anterior anchor in the patient as described below. Alternatively, there can be none, one, two or more than two graspable recesses, appendages, or structures on the top surface of the anchor. In the preferred embodiment, the anterior anchor body 42 is disc-shaped, but those of skill in the art will recognize that other embodiments are possible, as disclosed in U.S. Patent Application Publication No. 2004/0122456 which is herein incorporated by reference; note particularly the description of anchor structures. The anterior anchor can also be wholly comprised of or only partially comprised of one or more magnetic components. Alternatively, in other embodiments, the anterior anchor carries one or more weights within it such that gravity causes the intestinal walls to come together as a result of the weights within the anchors.

FIGS. 2C and 2D are cross sections of the anterior anchor of FIGS. 2A and 2B, taken along the line B-B in FIG. 2B. FIG. 2C shows the anterior anchor in its deployed configuration with the connector 12 of FIG. 1A passing through the hole or other passageway 44 in the body of the anchor. In the deployed configuration, the gripping elements 46 and teeth 50 engage the connector 12 with sufficient pressure to prevent movement of the anchor along the connector 12 in the direction of the arrow in FIG. 2C, which would increase the distance between the anterior anchor and posterior anchor (not shown). In the case where the connector is a suture, the surface of the suture can be roughend to enable gripping by the anchor. In FIG. 2D, the anterior anchor 40 is in its reduced profile configuration with the connector 12 of FIG. 1A passing through the hole or other passageway 44 in the body of the anchor. Preferably, the anterior anchor is made of a semi-rigid polymer which allows the anchor to be deformed into a substantially folded configuration illustrated in FIG. 2D. When in this configuration, the gripping elements 46 and teeth 50 do not significantly engage the connector 12. This allows movement of the anterior anchor 40 along the length of the connector 12 in the directions illustrated by the arrows in FIG. 2D. Once the anterior anchor is in the desired position along the connector 12, the anterior anchor is permitted to return to the configuration shown in FIG. 2C, and the gripping elements 46 and teeth 50 engage the connector 12, thus preventing movement between the connector 12 and the anterior anchor 40.

In an alternative embodiment, it is contemplated that the connector 12 can have notches 51, which interact with gripping elements 46 in a ratchet-and-pawl mechanism similar to that used in cable ties, providing a one-way adjustability, in which the posterior and anterior anchors can be moved toward each other, but not away from each other.

FIGS. 2E and 2F illustrate another embodiment of an anterior anchor 60 which is similar to the one illustrated in FIGS. 2C and 2D. In FIG. 2E, the gripping elements 62 and teeth 64 are oriented so that the anterior anchor can be deformed such that the top surface of the anchor is folded inward as illustrated in FIG. 2F. This is in contrast to the embodiment illustrated in FIG. 2D where the bottom surface of the anchor is folded inward. The teeth 64 in FIG. 2E are angled toward the top surface of the anterior anchor and engage the connector 12 of FIG. 1A such that they prevent movement of the anterior anchor along the connector 12 in the direction of the arrow in FIG. 2E, which would increase the distance between the anterior anchor and posterior anchor (not shown).

Figure 2G:
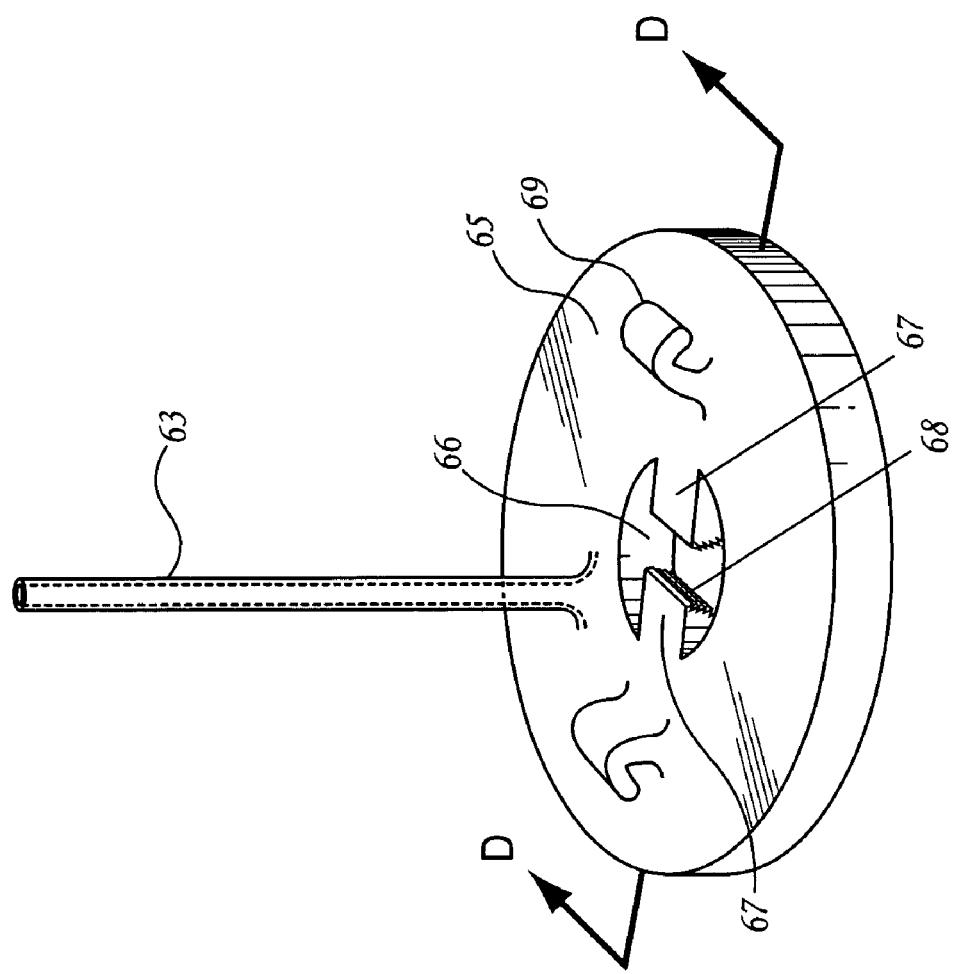
FIG. 2G is a perspective view of an inflatable embodiment of an anterior anchor.

FIG. 2G is a perspective view of a preferred embodiment where the anterior anchor is inflatable. The anterior anchor has a hollow, inflatable disc-shaped body 65 with a hole or other passageway 66 substantially in the middle of the body. Two gripping elements 67 project into the center of the hole or other passageway, although there can be as few as one or more than two gripping elements. The gripping elements can have teeth 68 angled toward the top surface of the anchor. Alternatively, in a preferred embodiment, the gripping elements are in the form of a rough surface rather than the protruding elements as shown in FIG. 2G. Such a surface, which may be a sandpaper-like surface, creates enough friction to prevent movement in either direction along the connector. Optionally, two hooks 69 are located on the top surface of the anterior anchor. Hooks 69 facilitate grasping by a surgical instrument during deployment of the anterior anchor in the patient as described below. Alternatively, rather than hooks, there can be one or more graspable protrusions on the body. In yet another embodiment, there are no hooks or graspable protrusions, and the body of the anchor is grasped directly to manipulate the anchor. In another embodiment, protrusions 69 are magnetic or otherwise sticky (e.g. Velcro) in nature to facilitate attachment to a surgical instrument.

An inflation tube 63 is used to inflate and deflate the anterior anchor. This inflation tube may or may not have a valve. In one preferred embodiment, the anterior anchor is filled with gas or fluid through the inflation tube and the fluid is held inside the anchor through an external (e.g. stopcock) valve controlled by the operator. When the inflation tube is cut at the end of the procedure, the inflation line is crimped closed thereby locking the inflating substance inside the anchor. Alternatively, the shears used to cut the inflation line can be metal and an electrocautery current can be applied through the shears and to the inflation line to weld it closed.

Figure 2H:
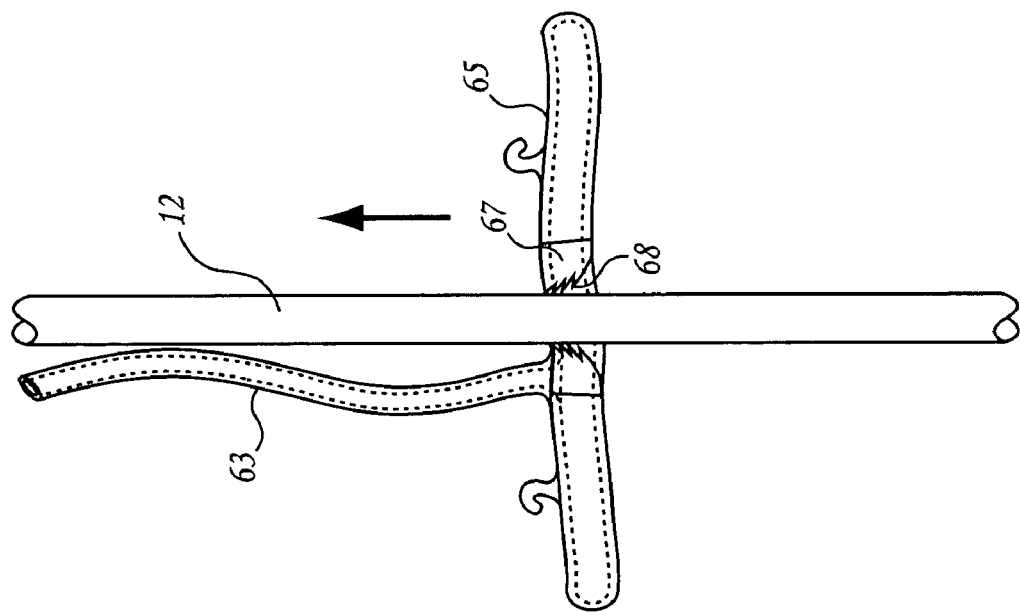
FIGS. 2H and 2I are side sectional views of the embodiment of the anterior anchor of FIG. 2G, taken along the line D-D in FIG. 2G, in its deployed and reduced profile configuration, respectively.
Figure 2I:
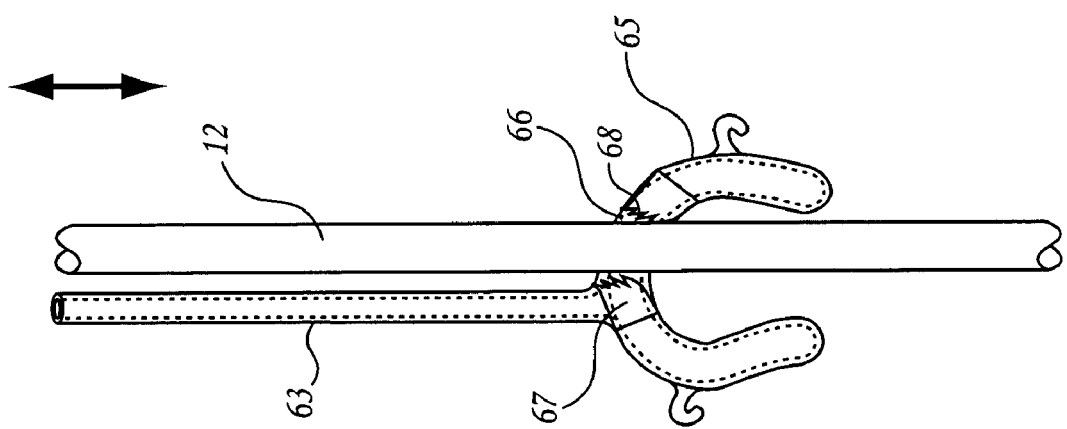

FIGS. 2H and 2I are cross sections of the anterior anchor of FIG. 2G, taken along the line D-D in FIG. 2G. The disc-shaped body 65 is readily deformable when in its reduced profile (i.e., uninflated) configuration as shown in FIG. 2I. The body can be inflated with a substance delivered through the inflation tube 63. When anchor body is inflated, the anchor assumes its deployed (i.e. inflated) configuration as shown in FIG. 2H with the connector 12 of FIG. 1A passing through the hole 66 in the body of the anchor. In the deployed configuration, the gripping elements 67 and teeth 68 engage the connector 12 with sufficient pressure to prevent movement of the anchor along the connector 12 in the direction of the arrow in FIG. 2H, which would increase the distance between the anterior anchor and posterior anchor (not shown). Alternatively, rather than defined gripping elements and teeth, the surface of body which defines the sides of the hole or other passageway 66 can be configured such that when the anchor body is inflated, the sides of the hole or other passageway expand to substantially close off the hole or other passageway and limit movement of the anchor relative to the connector through friction between the connector and the anchor.

In FIG. 2I, the anterior anchor 65 is in its reduced profile (i.e. uninflated) configuration with the connector 12 of FIG. 1A passing through the hole 66 in the body of the anchor. When in this configuration, the anchor body is readily deformable and the gripping elements 67 and teeth 68 do not significantly engage the connector 12. This allows movement of the anterior anchor 65 along the length of the connector 12 in the directions illustrated by the arrows in FIG. 2I. Once the anterior anchor is in the desired position along the connector 12, the anterior anchor is inflated by a filling substance delivered through the inflation tube 63, and the anchor assumes its deployed (i.e. inflated) configuration as shown in FIG. 2H; the gripping elements 67 and teeth 68 engage the connector 12, thus restricting movement of the anterior anchor 65 in one or both directions along the length of the connector 12. The filling substance can be a gas, liquid, or material which changes phase with time (i.e. it may harden, cure, polymerize, or become a gel with time).

Figure 3C:
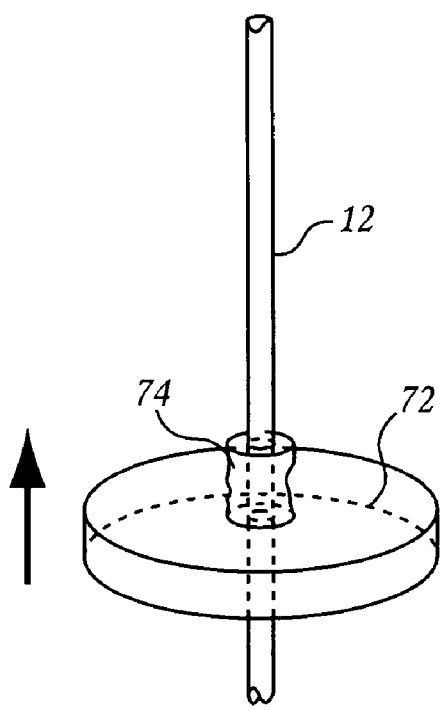
FIGS. 3B and 3C are perspective views of the embodiment of the anterior anchor shown in FIG. 3A in its reduced profile and deployed configuration, respectively.
Figure 3D:
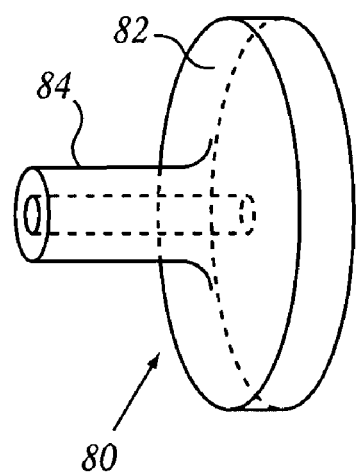
FIG. 3D is a perspective view of another embodiment of an anterior anchor.
Figure 3B:
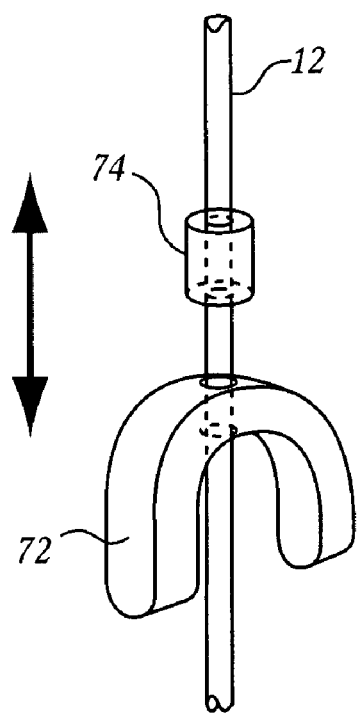
Figure 3A:
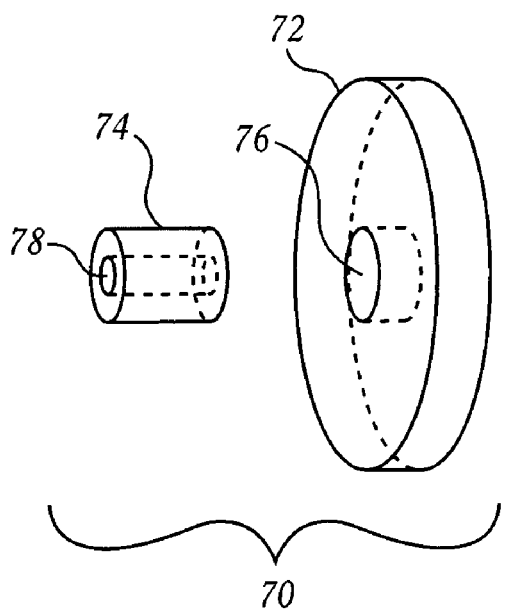
FIG. 3A is a perspective view of another embodiment of an anterior anchor.

FIG. 3A illustrates another embodiment of an anterior anchor 70 consisting of two parts, an anchor body 72 and a readily deformable collar 74. The anchor body and collar have a central hole or other passageway (76 and 78 respectively) through which the connector can pass. Preferably, the anterior anchor body is made of a semi-rigid polymer which can be deformed into a folded configuration with a reduced profile as illustrated in FIG. 3B. Preferably, the readily deformable collar 74 is permanently deformable; i.e., once deformed, it does not return to its original shape. As illustrated by the arrow in FIG. 3B, both the collar 74 and anchor body 72 can move along the connector 12 of FIG. 1A. Once the anchor body 72 is in the desired position, the collar 74 is crushed, such that the collar 74 engages the connector 12 and can no longer move along the length of the connector 12. This prevents the anchor body 72 from moving along the length of the connector 12 in the direction of the arrow illustrated in FIG. 3C, which would increase the distance between the anterior anchor and posterior anchor (not shown). FIG. 3D illustrates an alternative embodiment of the anterior anchor 80, where the anchor body 82 and deformable collar 84 are a single piece.

In a preferred embodiment, the anterior anchor is made from a biocompatible, radio- or magneto-opaque polymer, but it can also be made from various kinds of suitable materials known to those of skill in the art including metals, metal alloys, plastics, natural materials or combinations thereof as disclosed above. The anterior anchor can be solid, or alternatively, can be porous, mesh-like, umbrella-like or lattice-like. In a preferred embodiment, the anterior anchor is porous, mesh-like, umbrella-like or lattice-like to encourage fibrous ingrowth such that it becomes permanently attached to the stomach wall. Coatings can be added to the anchor, or a mesh material such as polypropylene can be fixed to the anchor surface, such that it touches the anterior stomach wall and encourages tissue ingrowth. In other embodiments, the anterior anchor is solid and treated to discourage tissue ingrowth with materials such as silicone, PTFE, or FEP which are generally hydrophobic and non-reactive. In other embodiments, the anterior anchor has a xenograft or allograft material attached to the anchor which ensures tissue ingrowth. In a preferred embodiment, the anterior anchor is disc-shaped and substantially flat, but those of skill in the art will recognize that other embodiments are possible.

Surgical Instruments

Figure 4A:
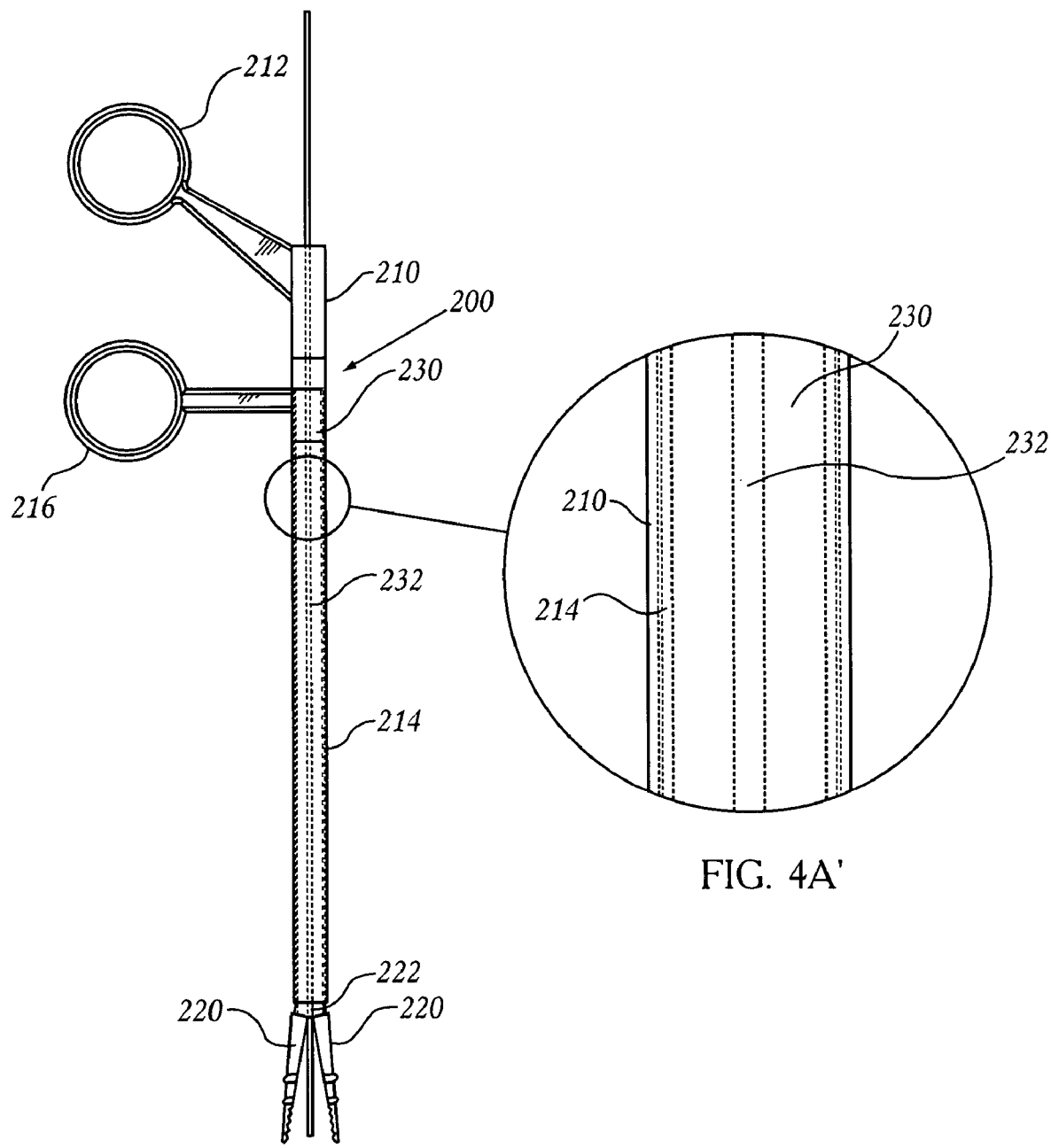
FIGS. 4A and 4A' are a side and blow-up view, respectively, of one embodiment of a tissue grasping instrument with the distal end in its open configuration.
Figure 4B:
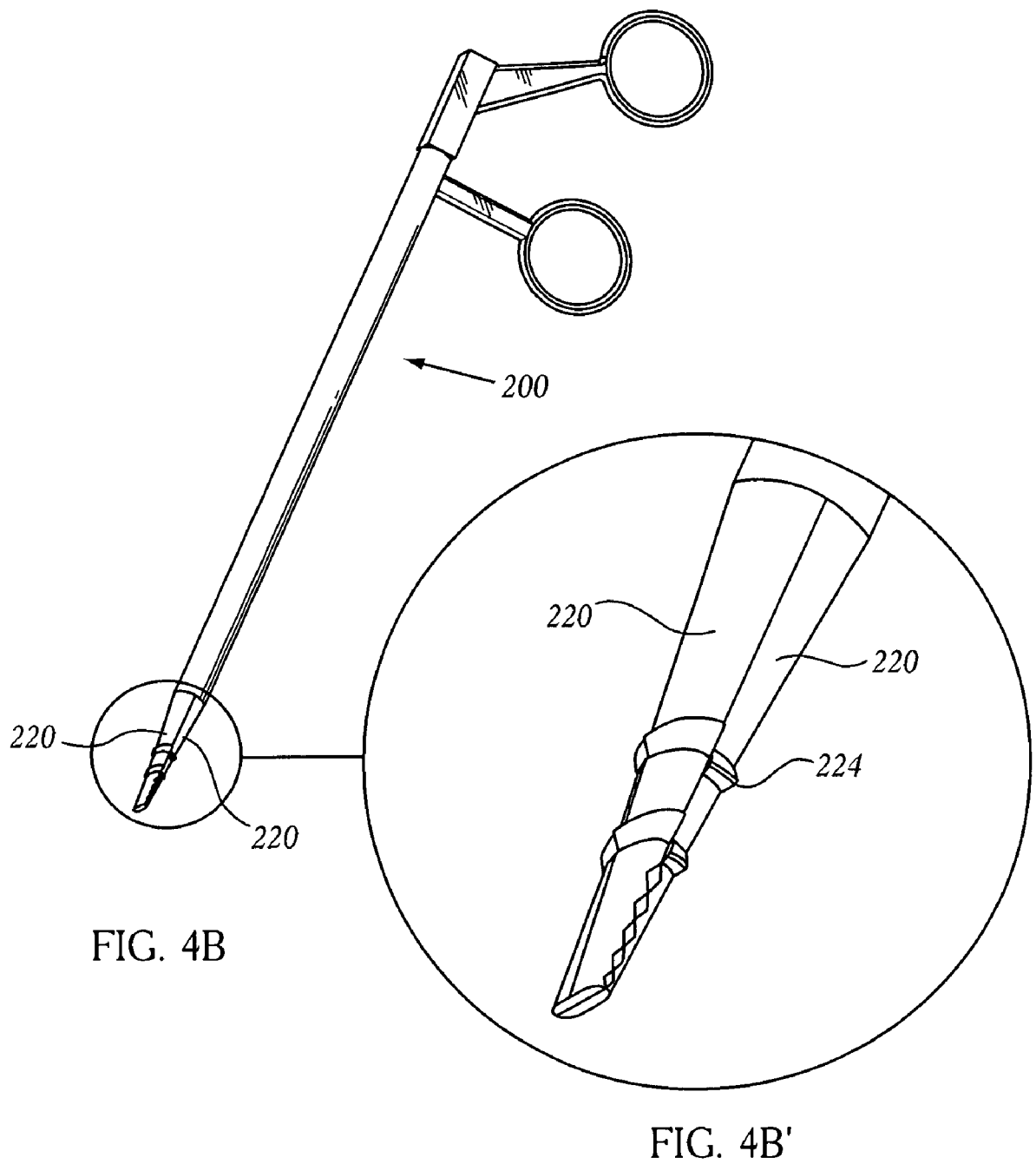
FIGS. 4B and 4B' are a perspective and blow-up view, respectively, of the tissue grasping instrument of FIG. 4A with the distal end in its closed configuration.

FIG. 4A illustrates one embodiment of a tissue grasping instrument 200. The tissue grasper has a tubular outer sleeve 210 to which a portion of a handle 212 is attached at the proximal end. As shown in more detail in the blow-up, FIG. 4A', disposed within the outer sleeve 210 is a tubular inner member 214 which has an outer diameter such that it can slide within the outer sleeve 210 in the longitudinal axis of the outer sleeve 210 but cannot move substantially transverse to the longitudinal axis of the outer sleeve 210. At the proximal end of the inner member, a second portion of a handle 216 is attached. At the distal end of the inner member is a pair of jaws 220 which is connected to the inner member at a hinge point 222. When the distal end of the inner member 214 is displaced from the inside of the outer sleeve 210 such that the hinge point 222 is outside the outer sleeve, the jaws 220 assume their open position as depicted in FIG. 4A. As the hinge point 222 is withdrawn into the outer sleeve 210, the outer sleeve forces the jaws 220 into their closed position, as illustrated in FIG. 4B. The opening and closing of the jaws 220 can be accomplished by manipulation of the handle portions 212 and 216.

Figure 4C:
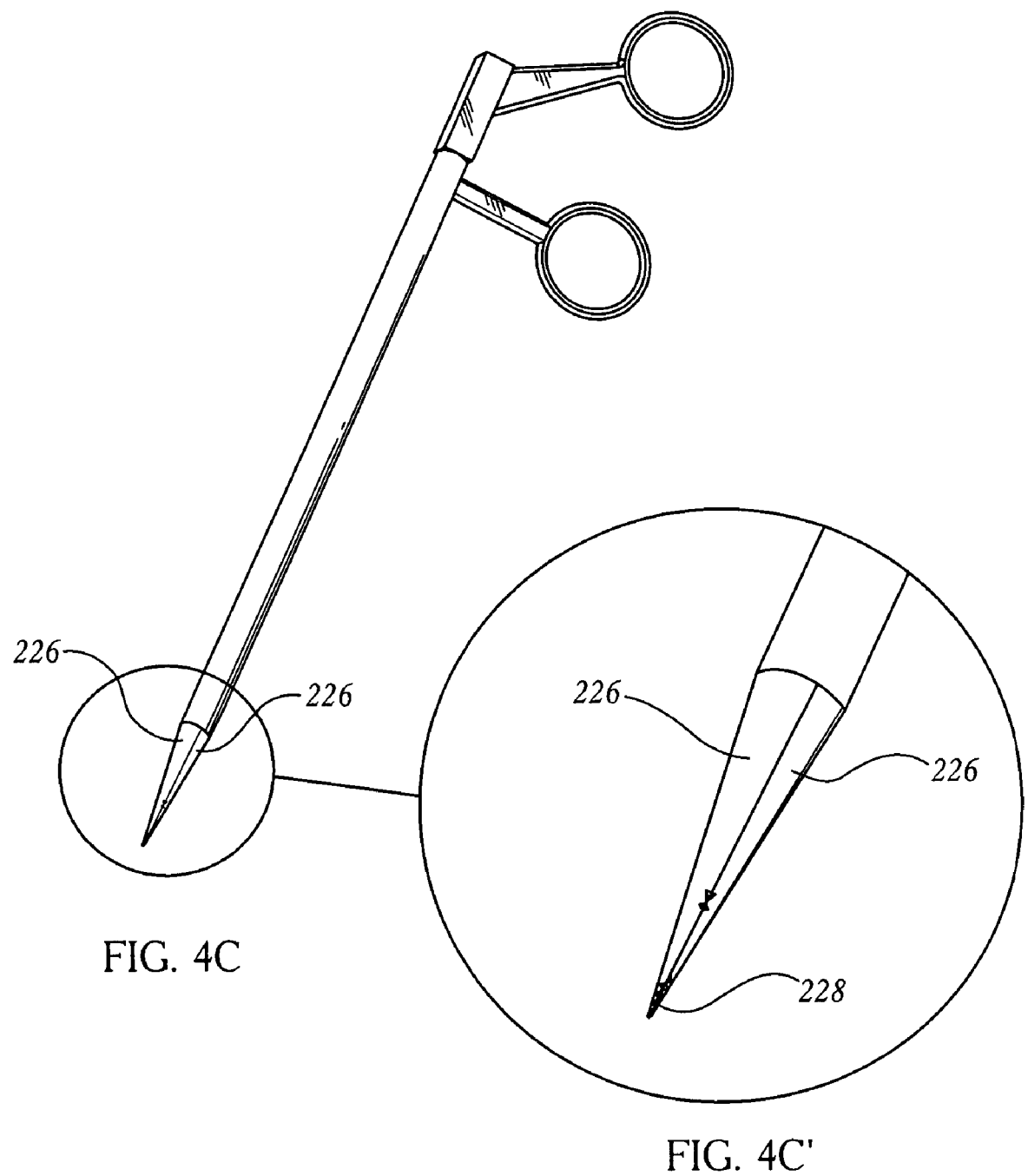
FIGS. 4C and 4C' are a perspective and blow-up view, respectively, of another embodiment of the tissue grasping instrument with the distal end in its closed configuration.

The distal end of the grasping instrument 200 is configured to cut, puncture, or dilate tissue when the jaws 220 are in the closed position. In one embodiment shown in FIG. 4B, the jaws 220 have screw-thread-shaped protrusions 224 on the surface. By rotating the instrument as it passes through tissue, the protrusions 224 facilitate the penetration of tissue, similar to a corkscrew. In another embodiment illustrated in FIG. 4C, the instrument has jaws 226 that form a sharp tip 228 when closed. In yet another embodiment, the jaws form a blade which can cut through tissues when in the closed position. One of skill in the art would recognize that the above configurations can be combined, or that other configurations are possible which facilitate the passage of the tip of the instrument through the wall of the stomach or other tissue.

It also should be realized to one skilled in the art that the closed end of the grasping device does not have to be the only instrument responsible for cutting through the tissue; the central lumen 230 of the device can be utilized to assist in tissue penetration. For example, a needle (e.g. a Veres needle) 232 can be passed through the lumen and the needle 232 can make the initial puncture through the tissue. The configuration of the distal end of the grasper is meant to be a tissue dilator and facilitator of the entry into the stomach after the needle makes the initial puncture. For safety, the needle can be retracted as the tissue grasper dilates the tissue.

In the embodiment of the tissue grasper 200 illustrated in FIG. 4A, the inner member 214 and outer sleeve 210 have a central tunnel 230 that extends the length of the tissue grasper. The tunnel 230 allows for the passage of an expanding means such as a needle 232, or other instrument or device such as the posterior or anterior anchor described above (see for example, the description above regarding the connector-suture combination in which the suture is left behind and the outer sheath of the connector is pulled away), through the length of the tissue grasper as shown in FIG. 4A. The central tunnel is also adapted such that a radially dilating sheath can be inserted through it. The diameter of the central lumen is preferably at least 4 mm, but can be at least 5, 6, 7, 8, 9, 10, 11, or 12 mm. In an alternative embodiment, the distal jaws can be configured to close through an electromechanical means or purely magnetic means such that the inner member is not necessary.

Figure 5A:
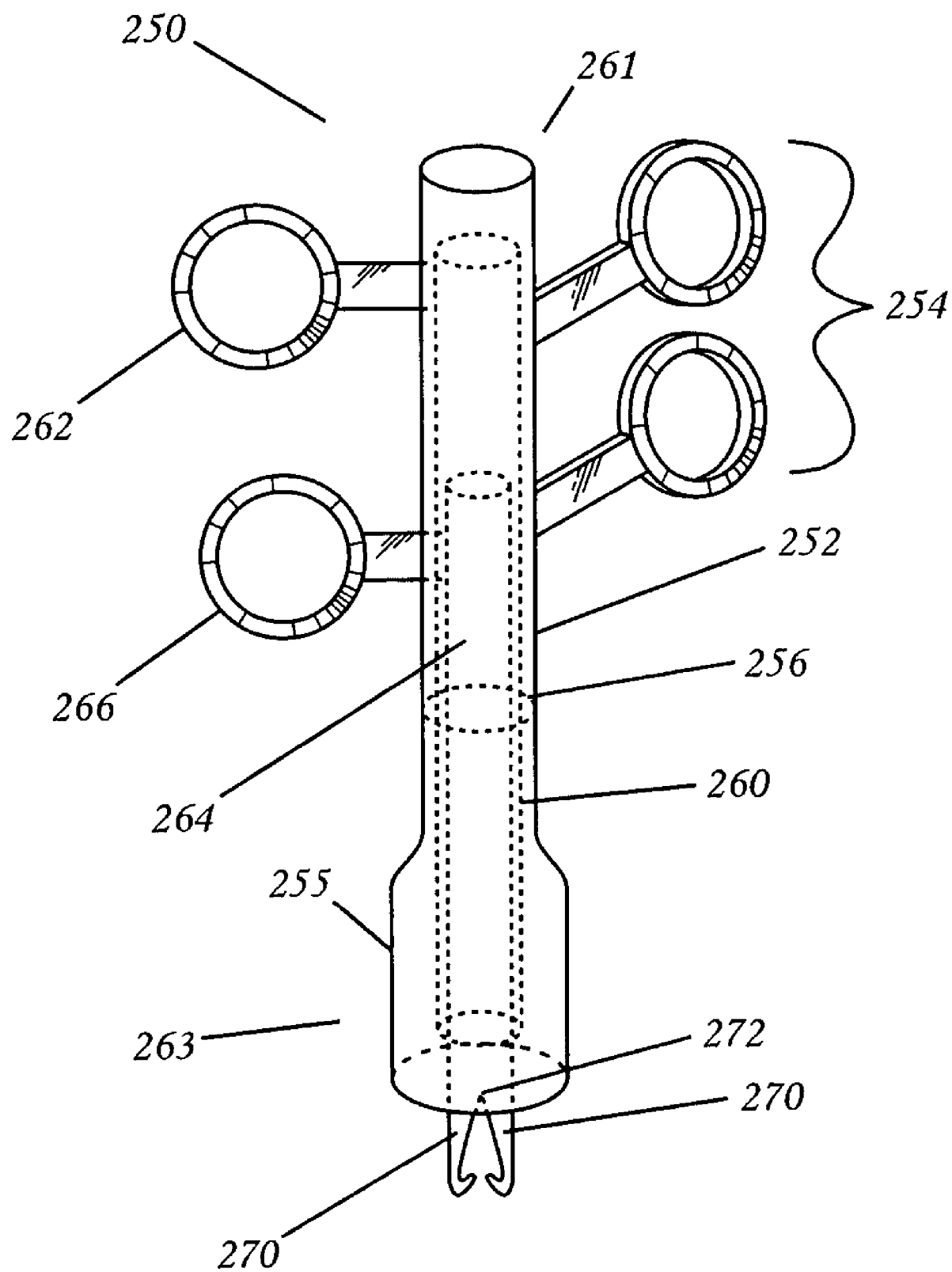
FIG. 5A is a side view of one embodiment of an anchor implantation instrument.

FIG. 5A illustrates one embodiment of an anchor implantation instrument 250 to implant the anterior anchor. The implantation instrument has a tubular outer sheath 252 which has a handle 254 attached. At the distal end, the outer sheath flairs out to an increased diameter 255 to accommodate the anterior anchor in its substantially folded position as illustrated in FIG. 5C. Within the outer sheath is an anchor grasping instrument 256 similar to the tissue grasping instrument of FIG. 4A, made up of a tubular middle sleeve 260 and a tubular inner member 264. The tubular middle sleeve 260 has an outer diameter such that it can slide within the outer sheath 252 in the longitudinal axis of the outer sheath 252 but cannot move substantially transverse to the longitudinal axis of the outer sheath 252.

The tubular middle sleeve 260 of the anchor grasping instrument has a portion of a handle 262 attached at the proximal end 261 of the instrument. Disposed within the middle sleeve 260 is a tubular inner member 264 which has an outer diameter such that it can slide within the middle sleeve 260 in the direction of the longitudinal axis of the middle sleeve 260 but cannot move substantially in transverse to the longitudinal axis of the middle sleeve 260. At the proximal end of the inner member, a second portion of a handle 266 is attached.

The distal tip 263 of the instrument is illustrated in more detail in FIGS. 5B and 5C, with the inclusion of the anterior anchor 40 of FIG. 2A and connector 12 of FIG. 1A. FIG. 5C is a side section view taken along the line C-C of FIG. 5B. At the distal end 263 of the inner member 264 is a pair of hooking members 270 which are connected to the inner member at a hinge point 272. When the distal end of the inner member 264 is displaced from the inside of the middle sleeve 260 such that the hinge point 272 is outside the middle sleeve, the hooking members 270 assume their open position as depicted in FIG. 5B. As the hinge point 272 is withdrawn into the middle sleeve 260, the middle sleeve forces the hooking members 270 into a closed position, as illustrated in FIG. 5C. The opening and closing of the hooking members 270 can be accomplished by manipulation of the handle portions 262 and 266.

The instrument is designed such that the anterior anchor is easily manipulated. When the anterior anchor is in its substantially folded or compressed configuration as in FIG. 5C, the entire anterior anchor assembly can be manipulated along the longitudinal axis of the connector 12. FIG. 5C depicts the assembly as it would be introduced over the connector 12 and into the patient. The operator pulls the connector 12 toward the operator such that the posterior anchor is urged toward the anterior anchor. When in position, the operator deploys anterior anchor 40. To deploy anterior anchor 40, outer sheath 252 is pulled back toward the operator. Middle sleeve 260 is then withdrawn proximally toward the operator as well. Hooking members 270 tend to fan out as the middle sleeve is pulled back and will release hooks 52. Once deployed, anterior anchor 40 is now fixed in a longitudinal position along the connector 12.

If the surgeon wants to readjust the anterior anchor, connector 12 is manipulated so that the hooks 52 of the anterior anchor are brought into contact with hooking members 270; middle sleeve 260 is advanced distally from the operator, permitting hooking members 270 to engage the hooks 52; such contact is facilitated by pulling back (proximally) on the connector 12. By manipulating the middle sleeve 260 over the hooking members 270, the hooks 274 on the ends of the hooking members 270 can engage the hooks 52 on the anterior anchor 40. The outer sheath 252 is then slid over the anterior anchor 40 (or the anchor-middle sleeve complex is withdrawn into the outer sheath 252), until it is compressed into an undeployed configuration as shown in FIG. 5C. As described above, when the anterior anchor 40 is in a substantially compressed configuration, it can move along the length of the connector 12 in either direction.

In an embodiment where an inflatable anterior anchor such as the one illustrated in FIGS. 2G-2I is utilized (or in the case that the anterior anchor is otherwise sufficiently compliant to be pushed through a laparoscopic port), a standard laparoscopic grasping instrument (with teeth) can be used to manipulate the anterior anchor. When the inflatable anterior anchor is in the uninflated position, it is sufficiently compliant such that it can easily be passed through a laparoscopic port prior to inflation and deployment or after it has been deflated for readjustment; the middle sheath may not be necessary because the compliance of the balloon enables easy compression into the outer sheath. The inflation tube 63 passes through the laparoscopic port and out of the patient. This allows the inflation tube 63 of the anchor to be temporarily opened or closed outside the patient allowing for deflation and reinflation until the anchor is in place. The inflation tube is then sealed and cut off, preferably substantially flush to the surface of the anterior anchor.

Implantation of the Transgastric Fastening Assembly

Figure 6B:
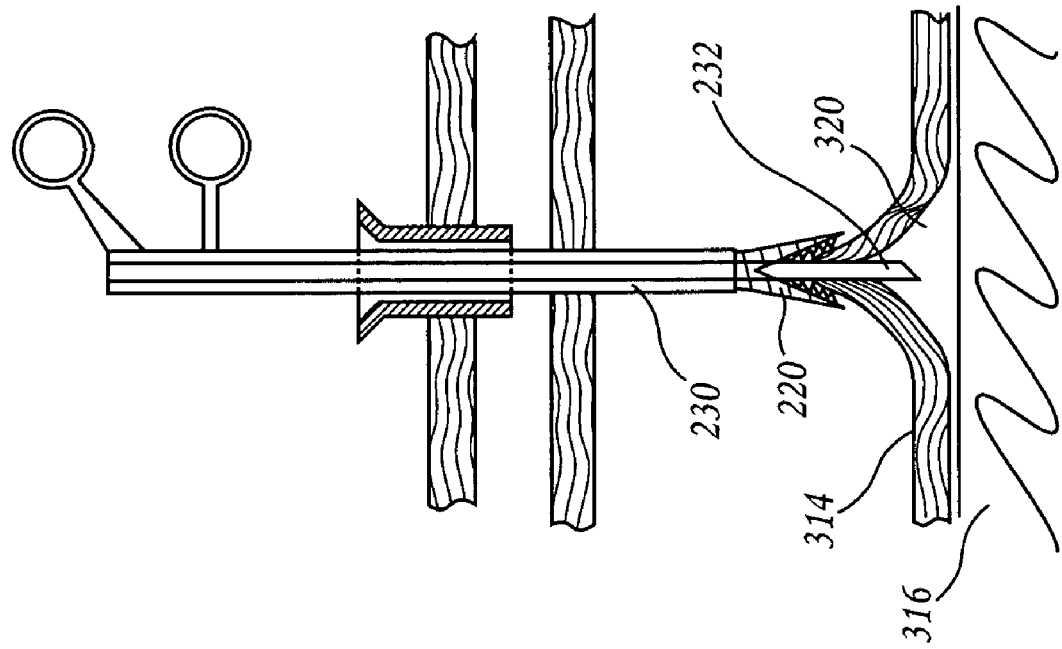
FIG. 6B illustrates the next step in one embodiment of a method of reducing the volume of the stomach. Shown is a side sectional view of a patient's abdomen with the instrument of FIG. 4 grasping the posterior wall of the stomach and a needle being inserted into the potential space of the lesser peritoneal sac.
Figure 6A:
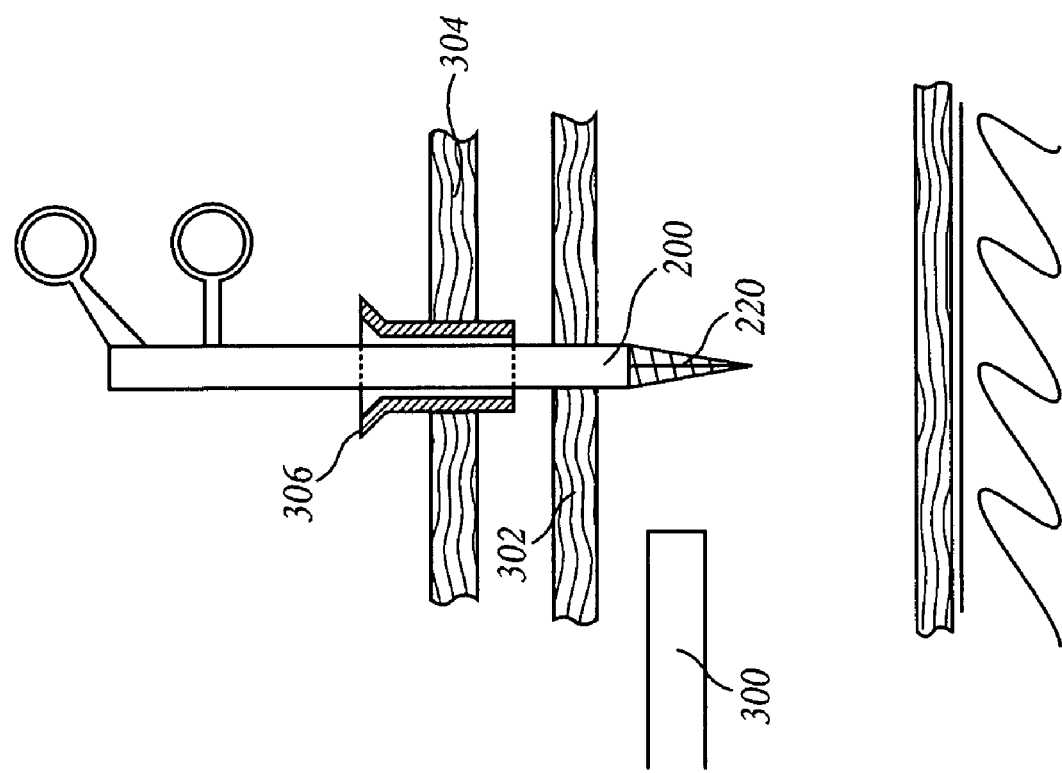
FIG. 6A illustrates the first step in one embodiment of a method of reducing the volume of the stomach. Shown is a side sectional view of a patient's abdomen with the instrument of FIG. 4 inserted into the patient's abdomen through a laparoscopic port.

FIG. 6A depicts the initial step of a preferred embodiment of a surgical method to implant the transgastric fastening assembly. The first part of the procedure, the "percutaneous procedure" involves entering the stomach with an endoscope 300 and insufflating the stomach with a gas. When insufflated, the anterior wall of the stomach 302 is pushed toward the anterior abdominal wall 304 to create a potential space (the stomach). After insufflation of the stomach, an incision is made in the skin and a standard laparoscopic port 306 is placed through the anterior abdominal wall 304 to a position wherein the distal end is in the potential space between the abdominal wall 304 and the anterior wall of stomach 302. The laparoscopic port 306 can be a radially dilating type port or similar port known in the art.

A particularly advantageous port is one which allows visualization (with a laparoscope) of the individual abdominal layers as it is being pushed through the abdominal wall (well known to those skilled in the art). Use of such a port allows the surgeon to "see" the different layers of the abdominal wall from within the trocar (using a standard laparoscopic camera) as the trocar is advanced through the abdominal wall. The endoscopic light inside the stomach will be "seen" by the surgeon as the port approaches the inner layers of the abdominal wall because the endoscopic light source transilluminates through the layers of the stomach wall and inner layers of the abdominal wall. Such visualization is advantageous if the patient has a very thick abdominal wall (e.g. in a morbidly obese patient) because the surgeon needs to ensure that another organ (e.g. the colon) is not positioned between the stomach and the posterior wall of the abdomen. Once the transillumination of the stomach is visible through the transparent port, the port 306 can be slipped in the abdomen between the abdominal wall and the anterior wall of the stomach. This portion of the procedure can be done without pneumoperitoneum and without general anesthesia. At this point, a camera can be placed inside the laparoscopic port to visualize the anterior wall of the stomach. Visualization of the surface of the stomach can also be achieved with this method and does not require general pneumoperitoneum. The camera can be slid along the stomach to reach virtually any portion of the anterior stomach or duodenal wall. Additional ports can also be placed in the space between the abdominal wall and the anterior wall of the stomach. At this point in the procedure, a therapeutic energy device can be applied to the stomach. For example, a laser, a radiofrequency device, a microwave device, or an ultrasound device can be applied to the stomach. Furthermore, electrical or nervous mapping can be performed with the surgical device in the position between the anterior wall of the stomach and the abdominal wall. In the embodiment where an extragastric balloon is being deployed (see below), such deployment proceeds at this step. Furthermore, in the embodiment where balloons are placed inside the stomach or neuro- or muscular stimulators or other devices are placed, they are implanted at this step and do note require general anesthesia and do not require general anesthesia.

In an alternative embodiment, "the laparoscopic procedure," a pneumoperitoneum is created through a separate incision in the skin. A veres needle, or other standard method to create a pneumoperitoneum (as is well-known to surgical practitioners) is used to insufflate the abdominal cavity.

In the percutaneous procedure, the tissue grasping instrument 200 of FIG. 4A is inserted through the port 306 with the jaws 220 in the closed position (with or without a needle projecting in front of the instrument) and is passed through the anterior wall of the stomach 302. When the jaws of the instrument are closed, the jaws define a sharp, dilating, and/or cutting configuration which can more easily advance through the stomach wall.

FIG. 6B depicts the next step in the percutaneous procedure. The jaws of instrument 200 are used to grasp the posterior wall of the stomach 314. The posterior wall of the stomach 314 is lifted away from the retroperitoneum 316, allowing for access to the potential space of the lesser peritoneal sac 320. A needle 232, such as a Veres needle (well-known in the art, a Veres needle allows for easy and safe access into and between two serosal layers), is inserted through the central channel 230 of the instrument and passed through the posterior wall of the stomach 314 into the potential space of the lesser peritoneal sac 320. The potential space of the lesser peritoneal sac 320 is expanded by injection of a gas, such as carbon dioxide, through the needle 232. In other embodiments, the potential space is expanded using a liquid, gel, or foam. Alternatively, the space can be expanded using a balloon or other space expanding or space filling device; alternatively, a surgical instrument (e.g. electrocautery and/or blunt ended grasper, etc.) can be used in place of a needle to access the lesser peritoneum or to expand the potential space of the retroperitoneum 320. Preferably, the expanded space of the lesser peritoneal sac can extend from the angle of His at the gastroesophageal junction to the pylorus.

In an alternative embodiment, the space is not expanded before the posterior anchor is placed. For example, in an embodiment where an inflatable posterior anchor is used, the potential space can be expanded by the anchor itself as it is inflated to its deployed configuration.

Figure 6D:
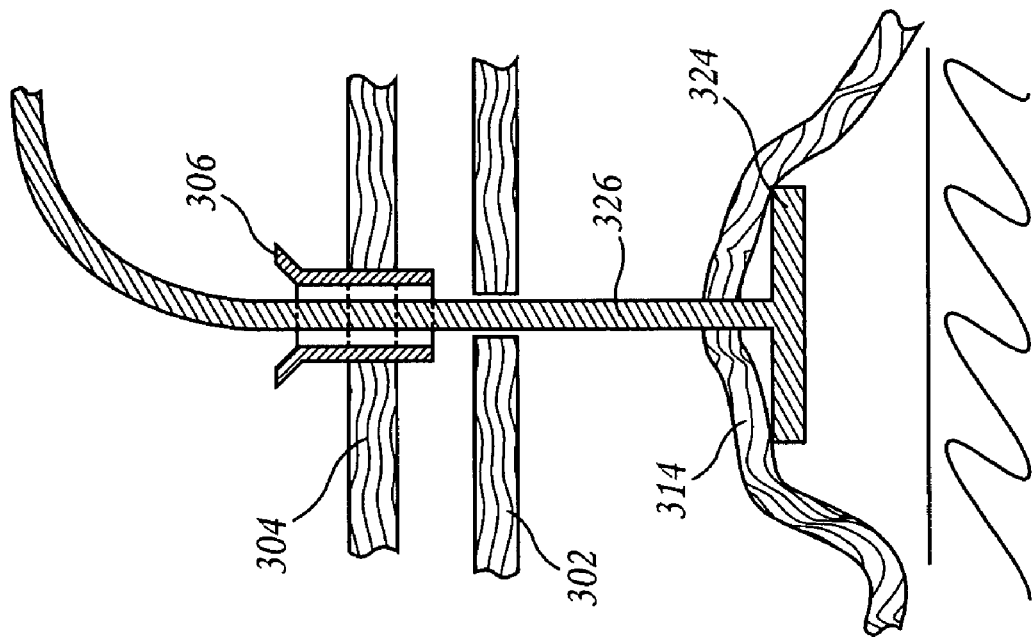
FIG. 6D illustrates the next step in one embodiment of a method of reducing the volume of the stomach. Shown is a side sectional view of a patient's abdomen with a posterior anchor and connector deployed in the expanded potential space of the lesser peritoneal sac, with the connector passing out of the patient's abdomen through a laparoscopic port.
Figure 6C:
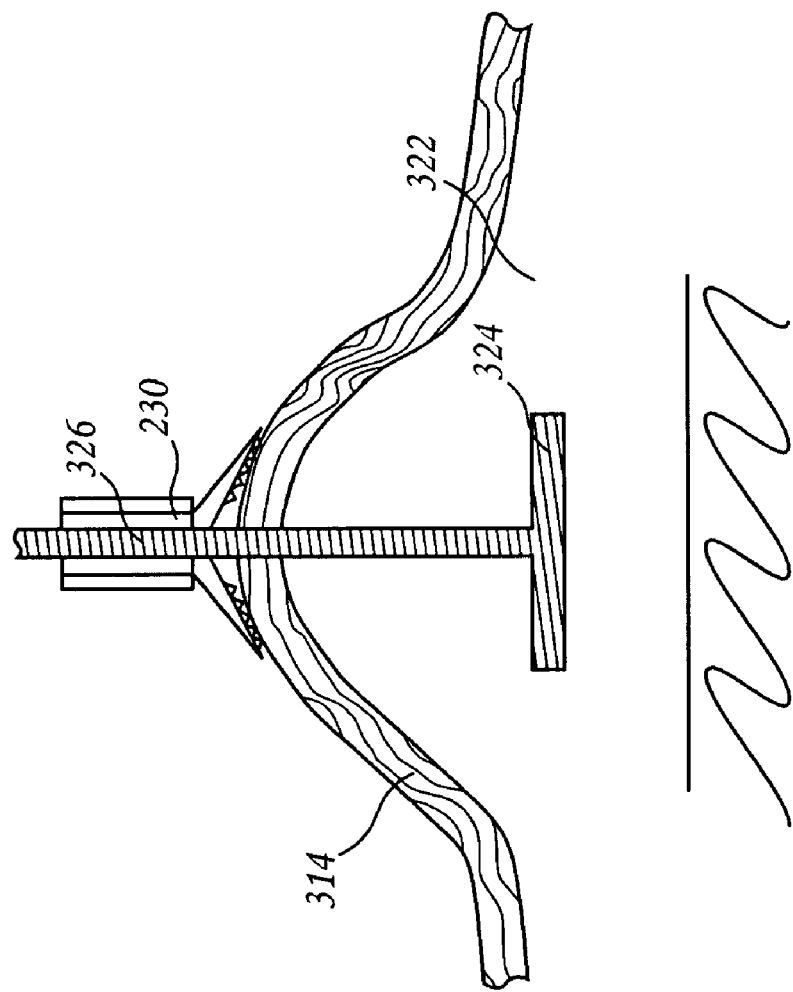
FIG. 6C illustrates the next step in one embodiment of a method of reducing the volume of the stomach. Shown is a side sectional view of a patient's abdomen with the instrument of FIG. 4 grasping the posterior wall of the stomach and a posterior anchor and connector deployed in the expanded potential space of the lesser peritoneal sac.

FIG. 6C depicts the next step in the "percutaneous procedure" embodiment. With a direct path from outside the patient to the lesser peritoneal sac 322, the needle 232 is withdrawn from the instrument 200. An optional dilation step can be performed at this stage in the procedure using a device such as a radially dilating sheath (e.g. InnerDyne STEP™ system; Sunnyvale, Calif.) inserted through the central channel 230 of the instrument. The dilating device expands the opening in the posterior wall of the stomach in such a way that the opening contracts down to a lesser profile after dilation. A posterior anchor 324 and connector 326, such as those depicted in FIGS. 1B, 1E or preferably 1F, in its reduced profile configuration, is passed through the central channel 230 of the instrument, through the posterior wall of the stomach 314, and deployed in the lesser peritoneal sac 322 as shown in FIG. 6C. Where the optional dilation step is performed, the posterior anchor 324 is passed through the dilating sheath. The connector 326 is preferably of sufficient length to pass from inside the lesser peritoneal sac 322 through the central channel 230 of the instrument and out of the patient's body. FIG. 6D depicts the deployed posterior anchor 324 and connector 326 after the grasping instrument is withdrawn from the patient and tension is applied to connector 326 to pull the posterior anchor 324 against the posterior wall of the stomach 314.

Figure 6E:
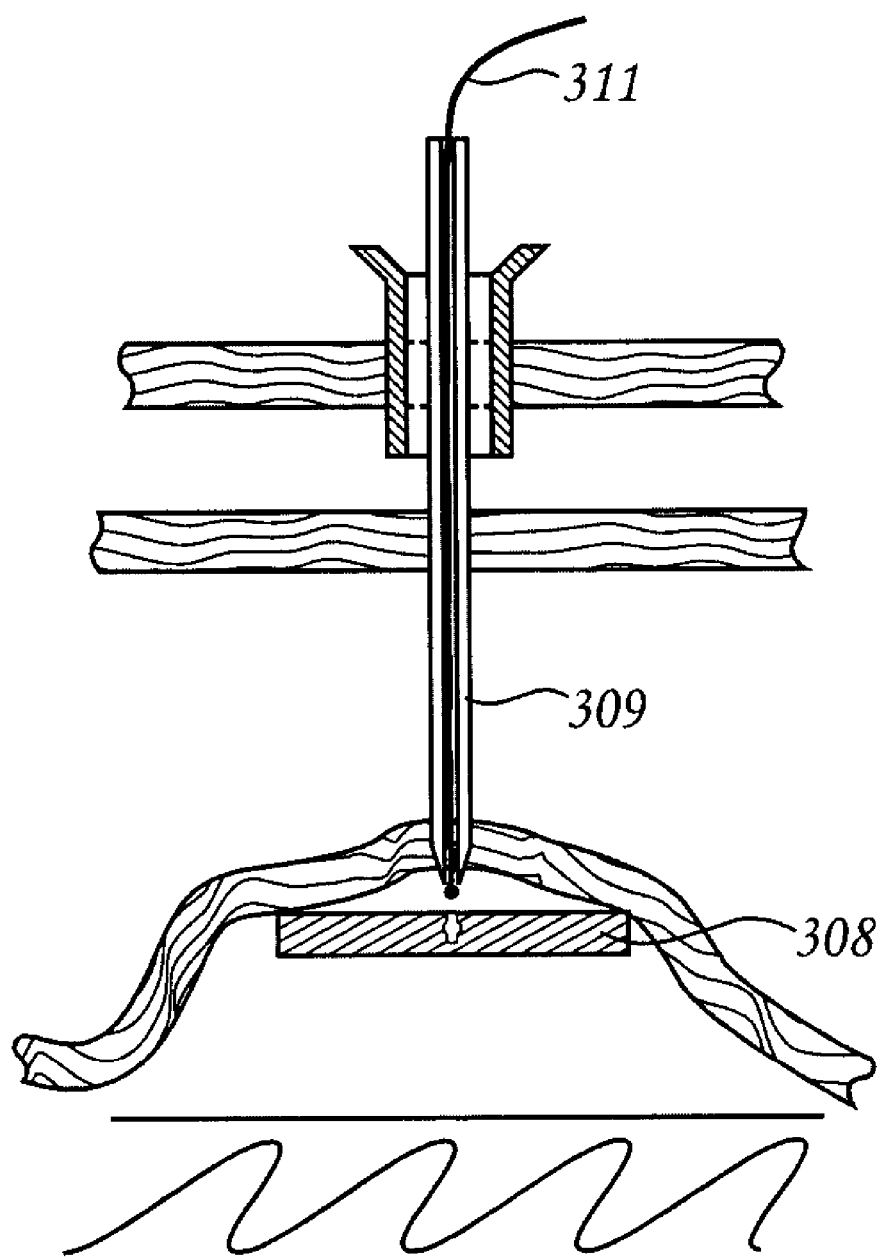
FIG. 6E illustrates an alternative step and device to place the posterior anchor in which the posterior anchor is brought behind the stomach before the connector is attached.
Figure 15A:
FIG. 15a illustrates the initial retrogastric step in the laparoscopic procedure.
Figure 15B:
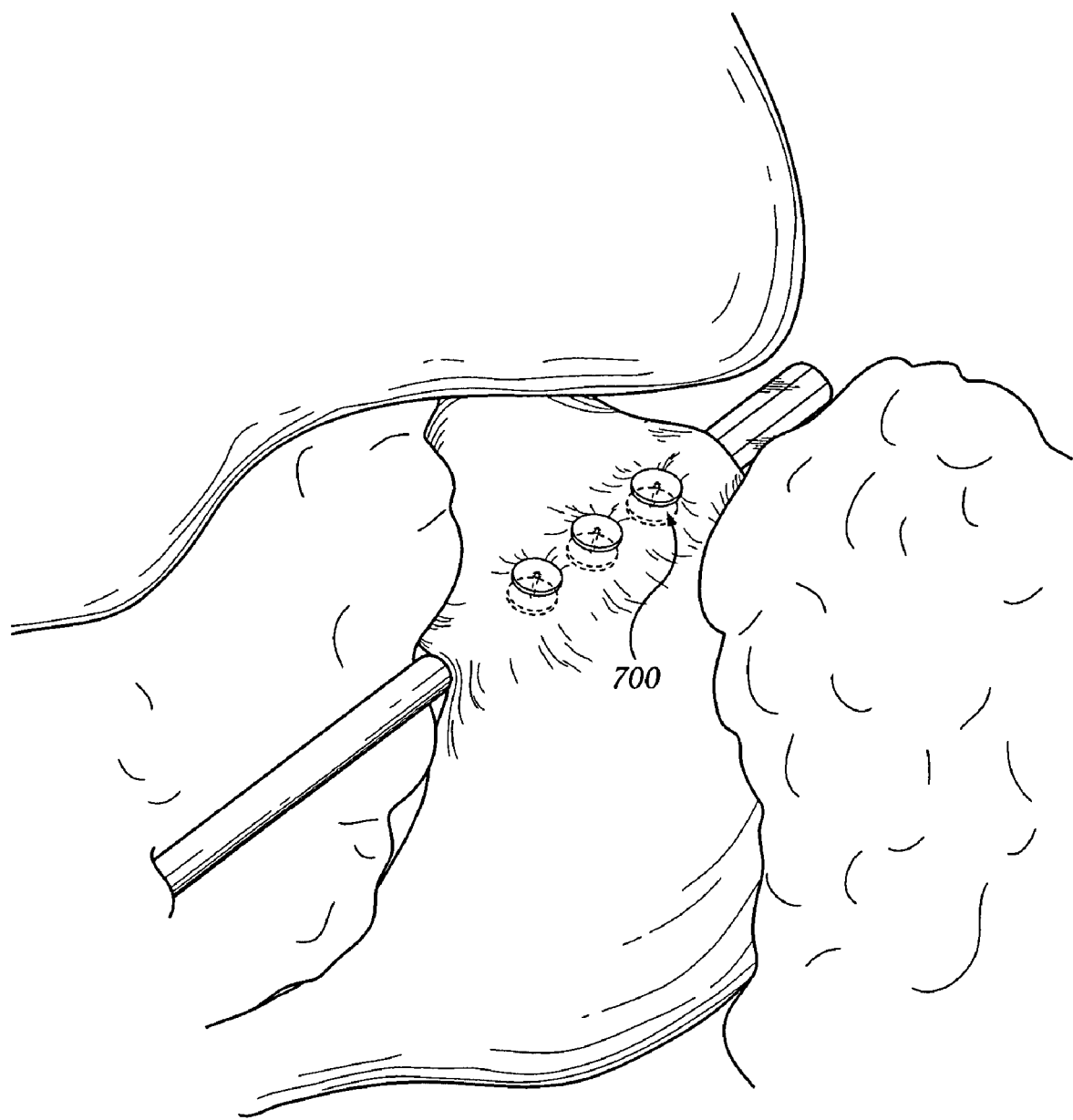
FIG. 15b depicts a horizontal row of transgastric anchors and connectors after placement in the stomach.
Figure 16:
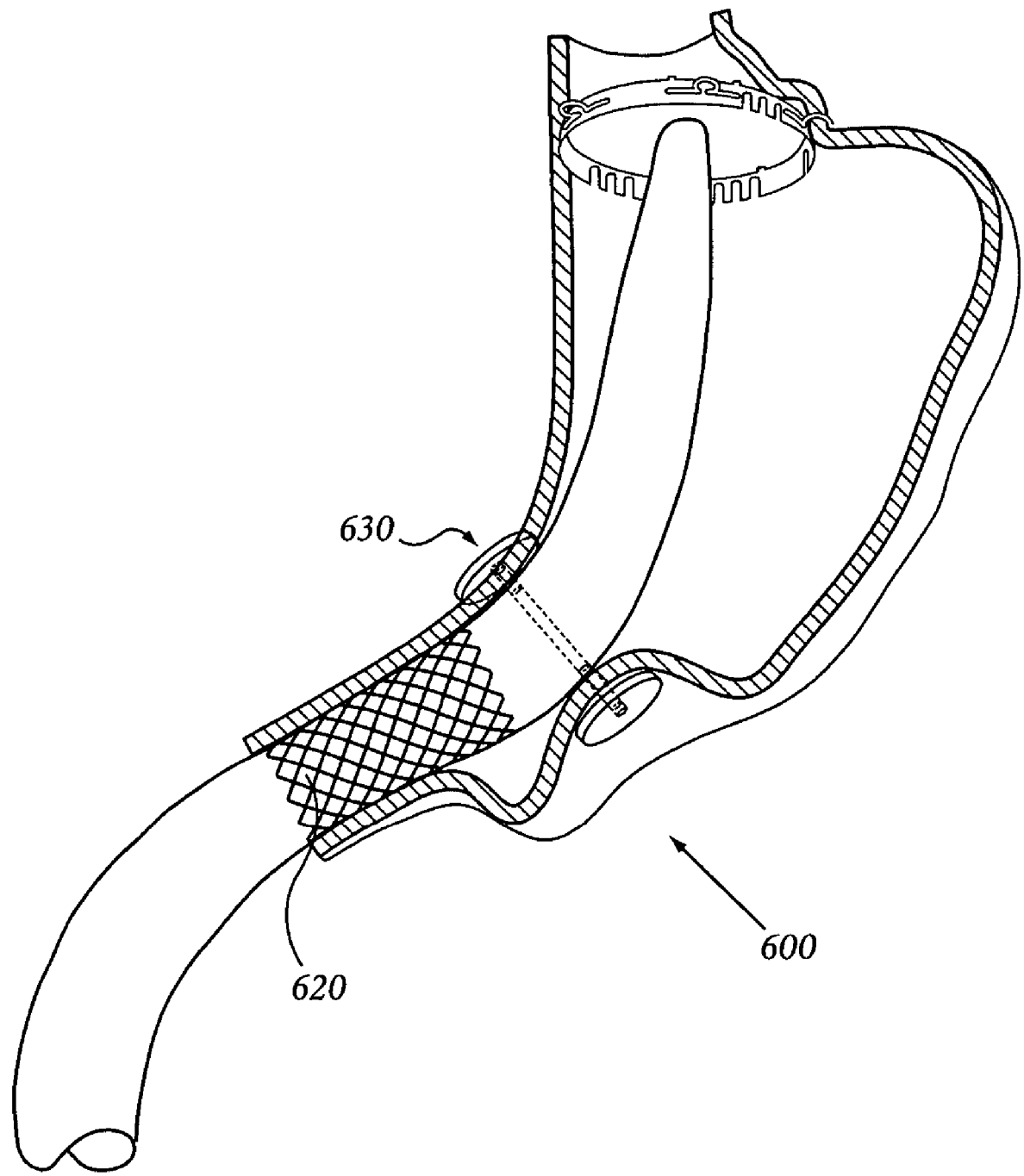
FIG. 16 depicts anchors of the present invention being used to secure an endoscopically placed gastric implant.

In the "laparoscopic embodiment," after insufflation of the abdominal cavity with a Veres needle, a retrogastric tunnel is created as is well known in the surgical art and is shown in FIG. 15a. The posterior anchors 510 are shown as a component of the retrogastric instrument in FIGS. 12 and 15a. The posterior anchors 308 are also shown in FIG. 6E. The suture-connector system 309, 311 depicted in FIG. 1H-J is also depicted in FIG. 6E and is used in one of the laparoscopic embodiments. Connector 309 engages anchor 308 and locks suture 311 into posterior anchor 308. Connector 309 is then slid over suture 311 prior to the anterior anchor (FIG. 13; 550) being slid over (tracking) the connector 311.

Figure 12:
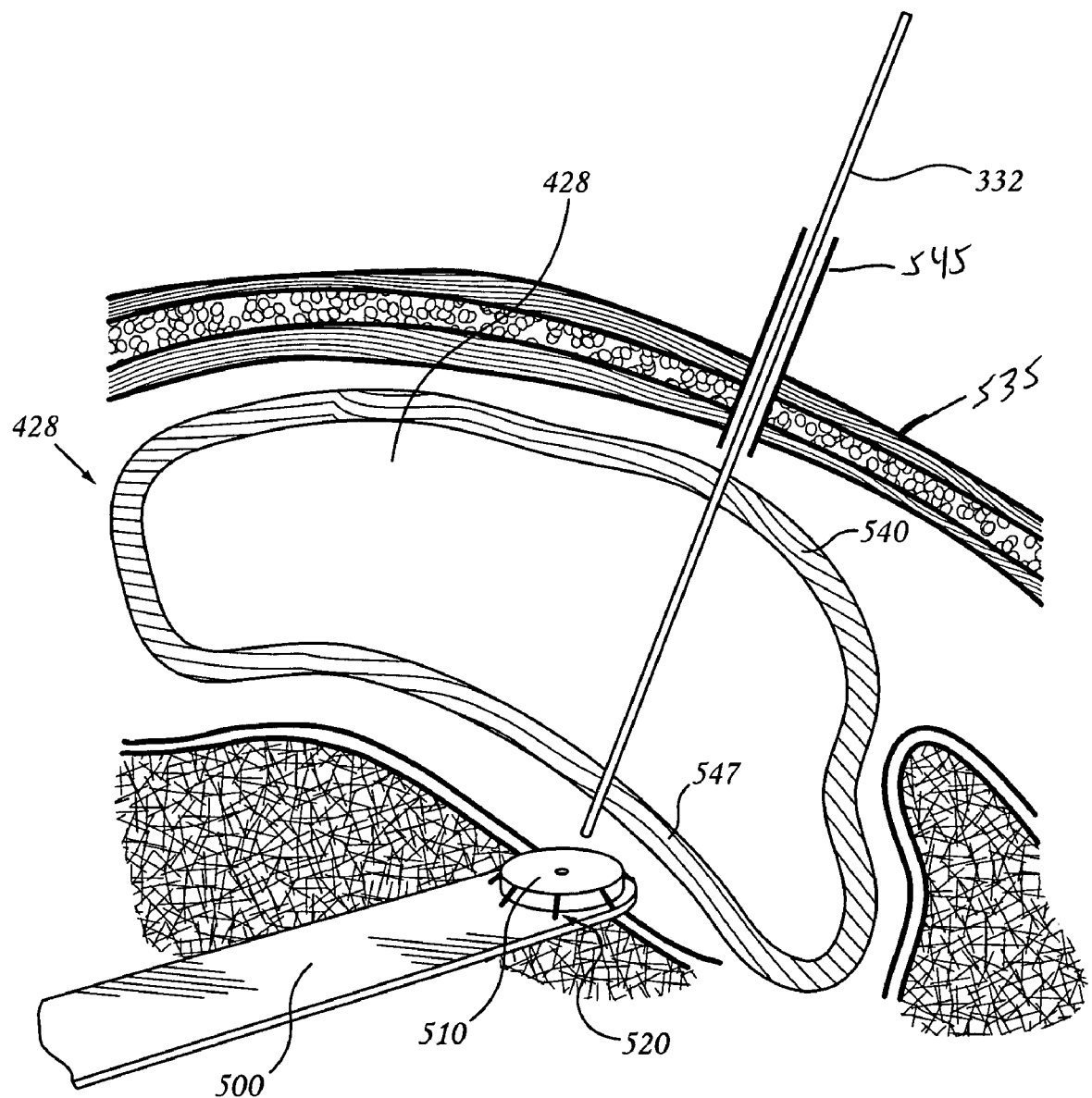
FIG. 12 illustrates another step in the laparoscopic method of placing a device in the stomach.
Figure 13:
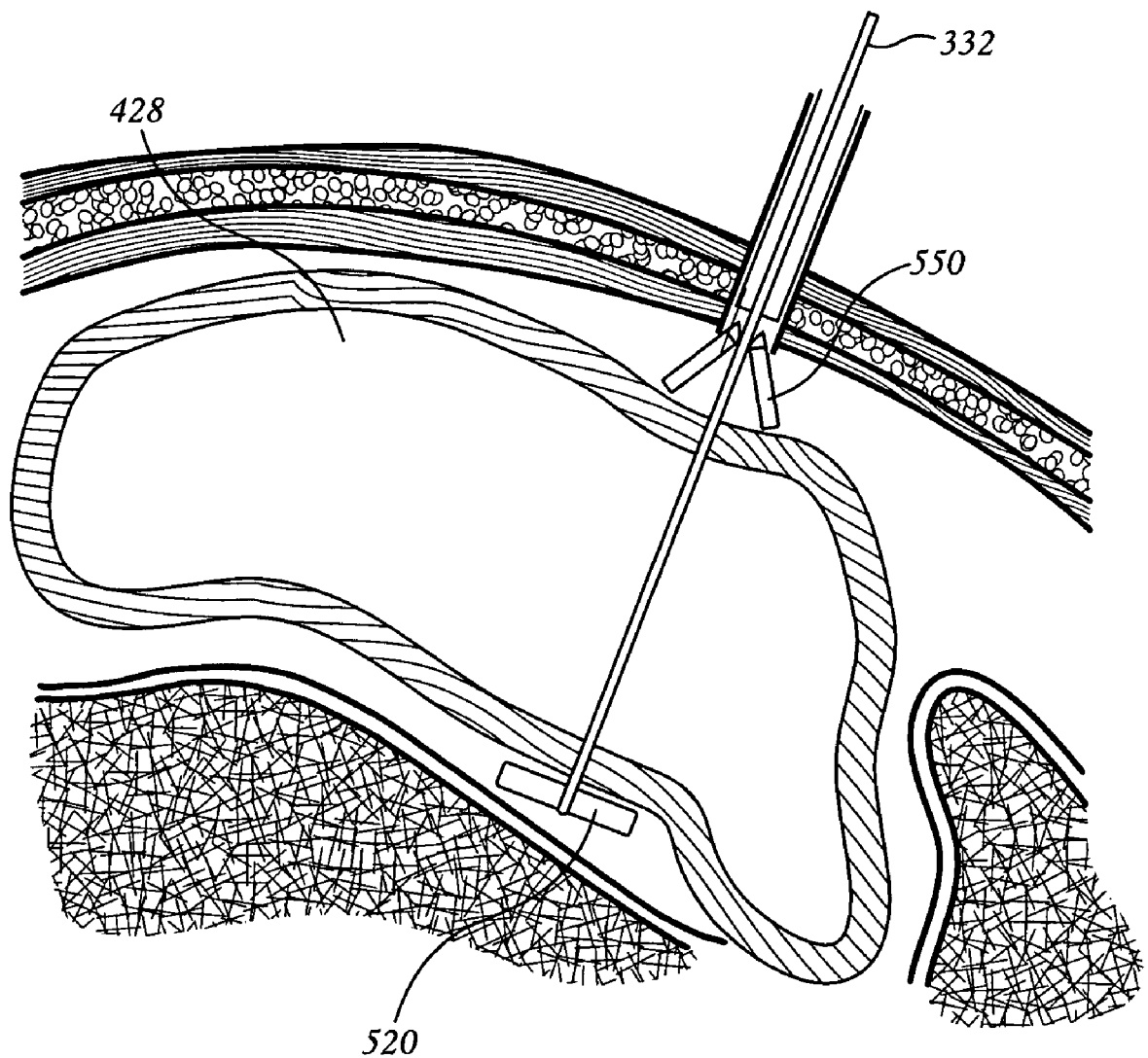
FIG. 13 illustrates another step in the laparoscopic procedure in which the anterior anchor is urged toward the posterior anchor over a connector.

FIG. 12 depicts one step in one laparoscopic embodiment; a laparoscopic instrument 500 is provided which has a reversibly attached anchor 510. Grips 520 reversibly grip anchor 510. Any of a variety of gripping mechanisms can be employed to retain the anchor 510 on laparosopic tool 500. Connector 332 is substantially similar to any of the connectors described above except that the posterior anchor 510 is not attached to connector 332 when it is inserted through the anterior abdominal wall. The surgeon places laparoscopic tool 500 behind the stomach 428 of the patient and connector 332 is advanced through lumen 545 formed in patient's skin 535 and anterior abdominal wall 530. Connector 332 is then further advanced percutaneously through first and second walls 540 and 547 of stomach 428.

When the connector 332 reaches the posterior anchor 510, gripping elements 520 are released by the surgeon through a mechanism which is integrated into the laparoscopic tool 500. Connector 332 is fixed to posterior anchor 510 through a locking mechanism. Mechanisms of locking connector 332 to posterior anchor 510 are well-known to those skilled in the art of mechanical fixturing. Some or all of the fixturing mechanisms may reside on the connector or on the anchor. In another embodiment, the gripping force of the grippers 520 can be overcome by force applied by the surgeon on connector 332. Mechanisms of locking other than mechanical also exist and include magnetic, electromagnetic, and adhesive means.

Figure 14:
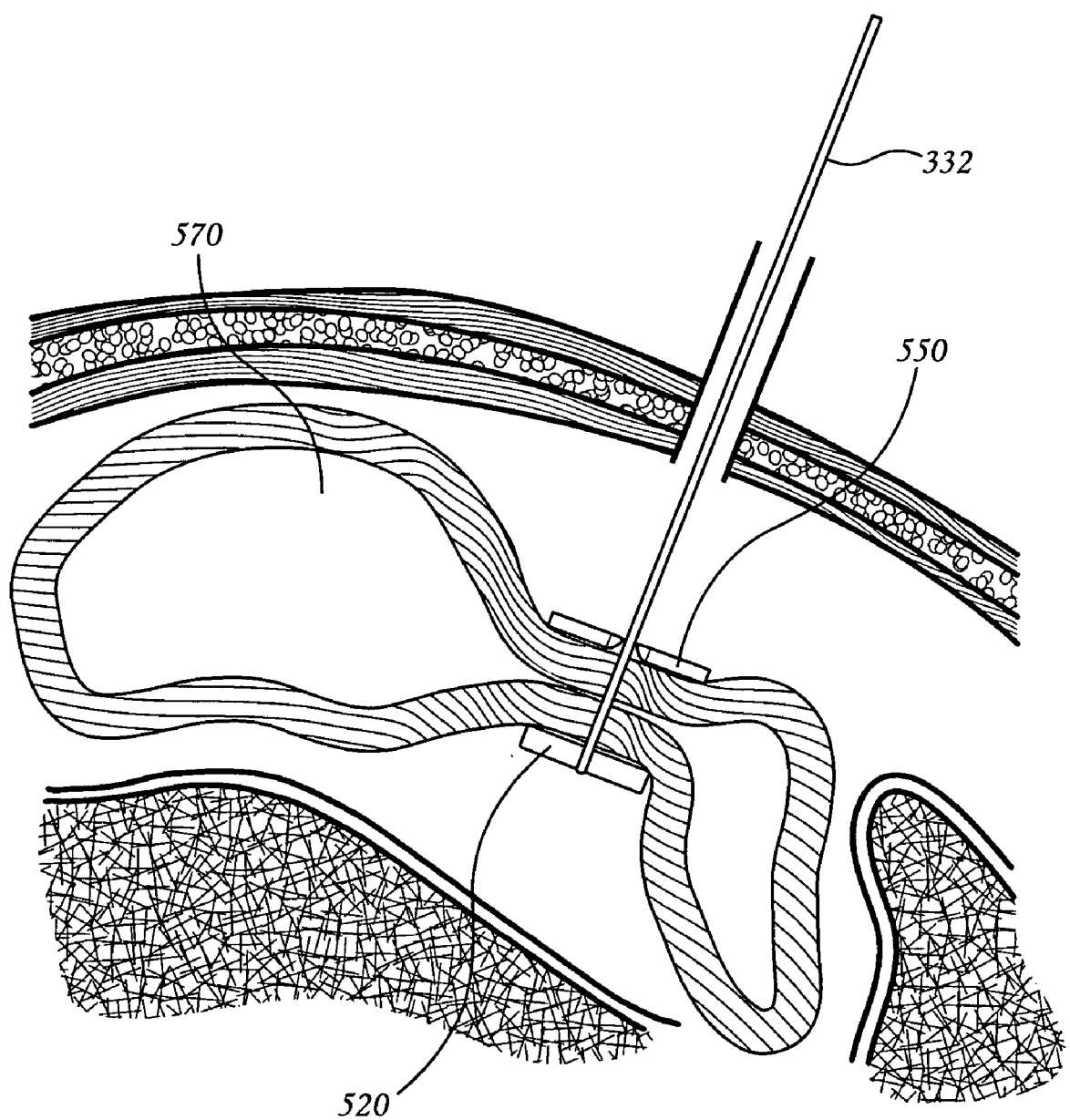
FIG. 14 illustrates another step in the laparoscopic procedure in which the anterior and posterior walls of the stomach are urged together.

An anterior anchor 550 (FIG. 13) is then placed over the connector 332 by the methodology and devices described in the next paragraph; the mechanism of deploying the anterior anchor is the same in both the "laparoscopic" and "percutaneous" procedures. The walls of the stomach are urged together (FIG. 14) to create a resistance to the flow of food within the stomach. 570 depicts one side of the stomach after the walls of the stomach are urged together. 570 is the side of the stomach where food enters. Its volume and capacity are now reduced as compared to its original volume and capacity. Although not shown, connector 332 is subsequently truncated at the level of the anterior anchor 550 after the anterior anchor is deployed and by any of the mechanisms described and depicted above.

Figure 7A:
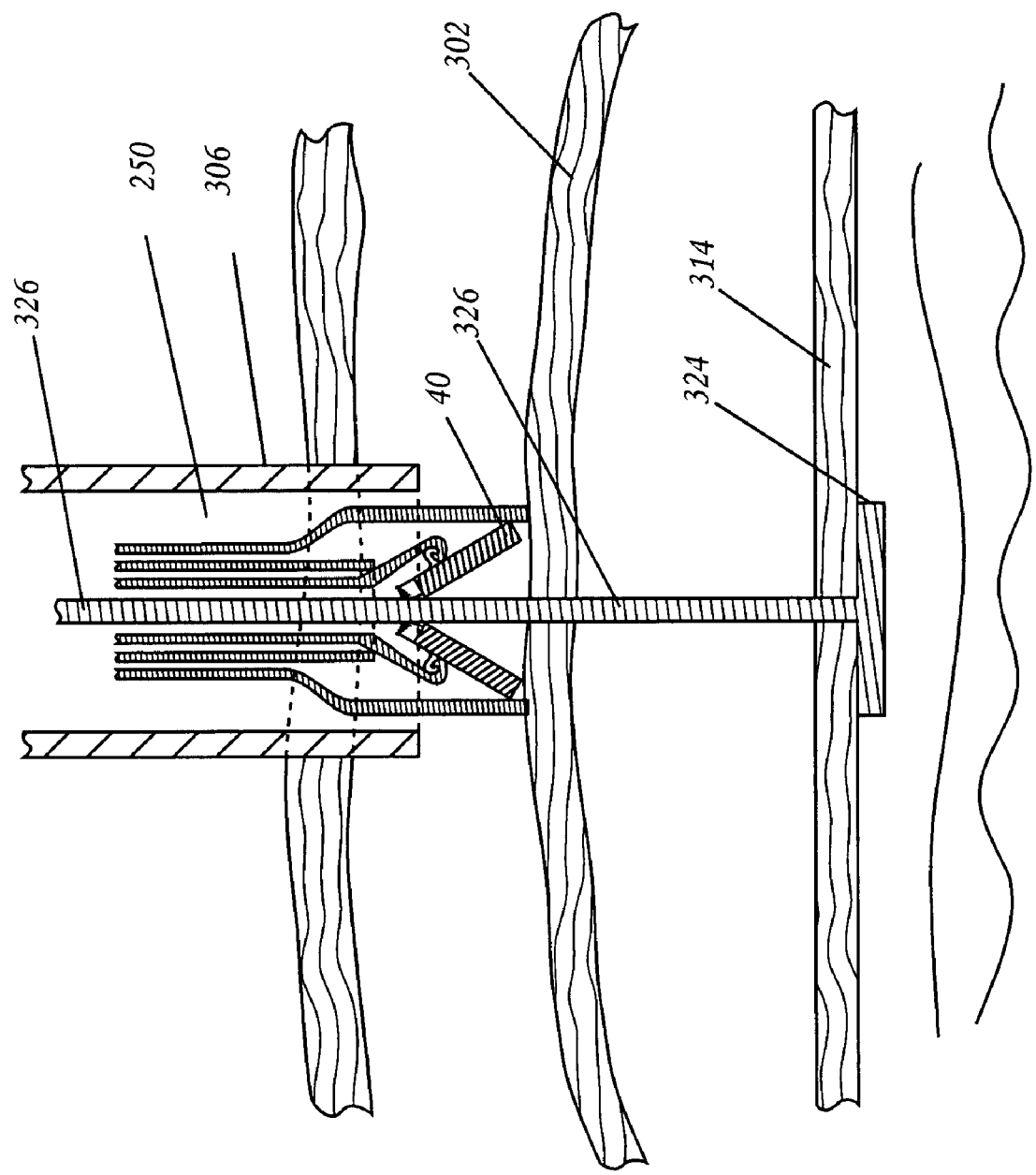
FIG. 7A illustrates the next step in one embodiment of a method of reducing the volume of the stomach. Shown is a side sectional view of a patient's abdomen with the instrument of FIG. 5C placing an anterior anchor in the patient's abdomen adjacent to the anterior wall of the stomach.

FIG. 7A illustrates the step of implanting the anterior anchor. The connector 326 is inserted through the hole or other passageway of an anterior anchor 40 of FIG. 5C, and the anchor implantation instrument 250 of FIGS. 5A, 5B and 5C is used to slide the anchor 40 through the laparoscopic port 306 into the abdomen of the patient. The anterior 302 and posterior 314 walls of the stomach are urged together, either by using the anchor implantation instrument 250 to urge the anterior wall 302 toward the posterior wall 314, or by pulling on the connector 326 and posterior anchor 324 to urge the posterior wall 302 of the stomach toward the anterior wall 314, or by a combination of the two methods. Once the anterior anchor 40 is in the desired position, the anterior anchor 40 is placed in its deployed configuration by manipulating the anchor implantation instrument 250 as described above.

In a preferred embodiment, the inflatable anterior anchor of FIGS. 2G-2I is used, and the use of the implantation instrument of FIG. 5C is optional. After the anterior anchor is in the desired position, the anterior anchor is inflated with a filling substance through the inflation tube until it is in its deployed configuration. The gripping elements 67 and teeth 68 are thus engaged against the connector 326. The anchor implantation device 250 can then be withdrawn from the patient's abdomen.

With the transgastric fastening assembly complete, the surgeon can examine the resulting configuration of the stomach using an endoscope. If the anterior anchor is not in the desired location, its placement along the connector can be adjusted as described above. Alternatively, in another embodiment, the anterior anchor can be urged closer to the posterior anchor simply by pushing it along the connector without using the implantation device to capture the anchor and deform it into its reduced profile configuration.

In another embodiment, the anterior anchor can be deflated, allowing the anterior anchor to be repositioned, and then reinflated to engage the connector. FIG. 7B illustrates the transgastric fastening assembly with the anterior anchor 40 in its deployed configuration on the connector 326 and the anchor implantation instrument removed from the patient's abdomen. The anterior 302 and posterior walls 314 of the stomach have been urged closer together by the transgastric fastening assembly. Whether the walls of the stomach are urged into contact or not is determined by the surgeon. Contact between the mucosal surfaces can be loose such that food can go through yet a significant resistance is provide; alternatively, mucosal surfaces are urged together to touch but food cannot pass through the apposition.

Figure 7C:
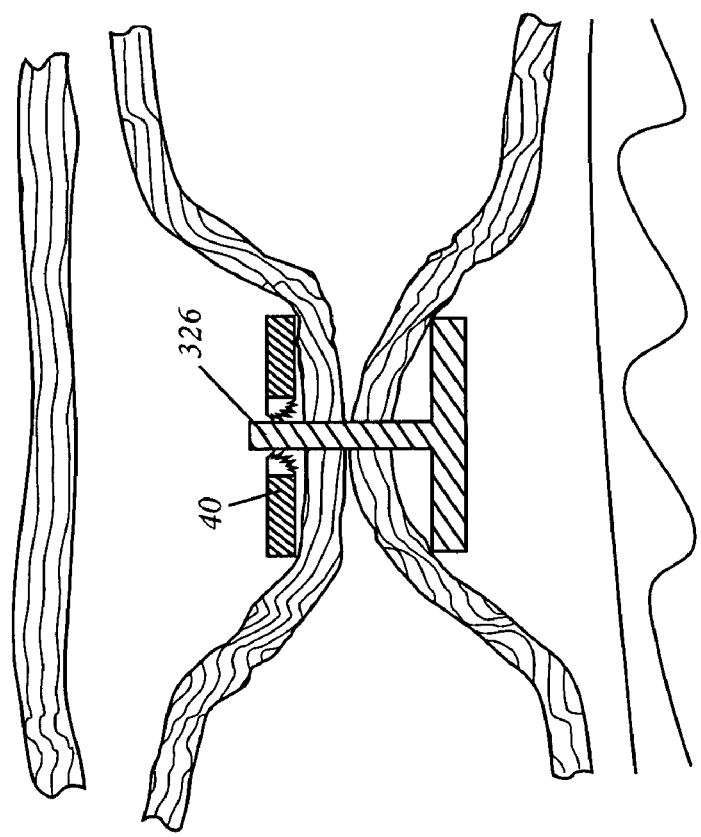
FIG. 7C illustrates the next step in one embodiment of a method of reducing the volume of the stomach. Shown is a side sectional view of a patient's abdomen after the connector has been cut flush with the anterior anchor.
Figure 7B:
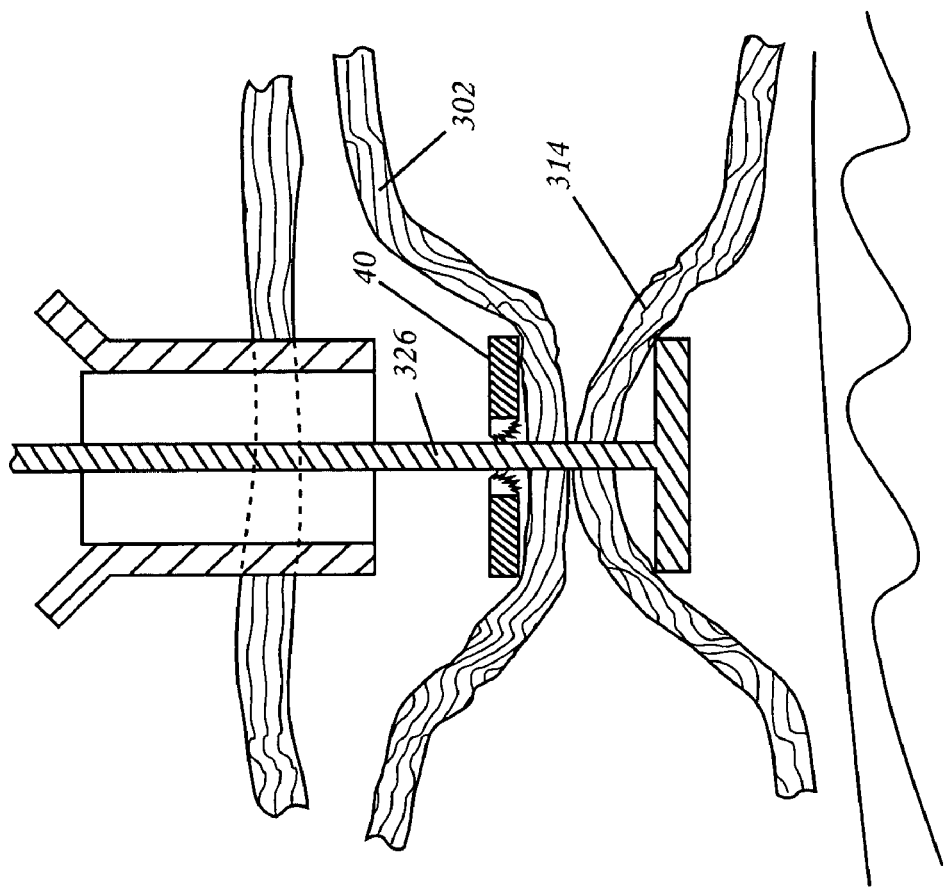
FIG. 7B illustrates the next step in one embodiment of a method of reducing the volume of the stomach. Shown is a side sectional view of a patient's abdomen with an anterior anchor in its deployed configuration on the connector, with the anterior and posterior walls of the stomach urged together.

FIG. 7C depicts a transgastric fastening assembly in its final configuration after deployment. Once the surgeon is satisfied that the transgastric fastening assembly is properly placed, a cutting implement, well-known to those of skill in the art, is inserted through the laparoscopic port and the connector 326 is cut, preferably flush to the anterior anchor 40. In some embodiments, the cutting instrument is placed over the connector (tracks) with the connector as a guide. In an embodiment, where inflatable anchors are used, the hollow connector and inflation tube are sealed prior to, or as a result of, cutting, preventing anchor deflation. Alternatively, if a filling substance which hardens with time is used, it may not be necessary to seal the connector or inflation tube prior to cutting if the filling substance is sufficiently hard or viscous such that it will not leak from the connector or inflation tube.

When more than one transgastric fastening assembly is to be implanted, it is sometimes preferred to insert all of the posterior anchors and connectors before attaching any or all anterior anchors; in some embdodiments, an instrument to measure tension is used to measure the compression of the stomach mucosa prior to the operation. This is in contrast to attempting to place one complete transgastric fastening assembly and then subsequent assemblies. While possible, if one were to place entire fastening assemblies in series, each successive assembly would be more difficult to place because the volume of the stomach would be progressively reduced resulting in more difficult visualization each time.

Figure 8A:
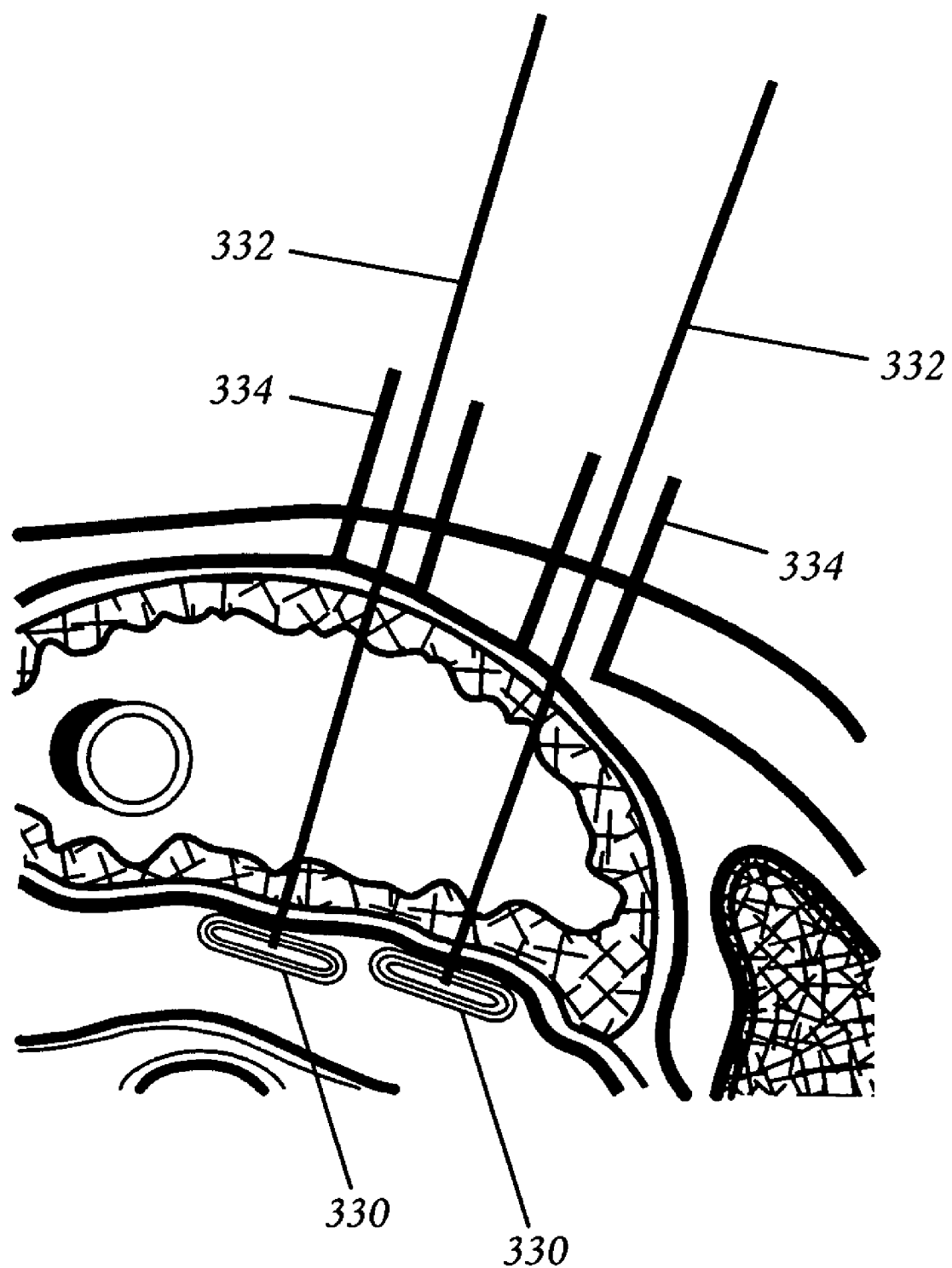
FIG. 8A illustrates an embodiment of a method of reducing the volume of the stomach. Shown is a side sectional view of a patient's abdomen after two posterior anchors and connectors have been deployed adjacent to the posterior wall of the stomach, with the connectors passing out of the patient's abdomen through laparoscopic ports.

FIG. 8A depicts an embodiment in which two posterior anchors 330 and connectors 332 are deployed in the expanded lesser peritoneal sac. In this embodiment, there is one laparoscopic port 334 for each connector 332. Alternatively, there may be more anchors placed than incisions and laparoscopic ports. Depending on how far apart the anchors are placed, a given laparoscopic port can be used to implant a plurality of transgastric implants. This can be accomplished because there is significant mobility of the stomach and/or abdominal wall which allows for different points along the anterior wall of the stomach to be accessed without having to create another hole through the abdominal wall.

Figure 8B:
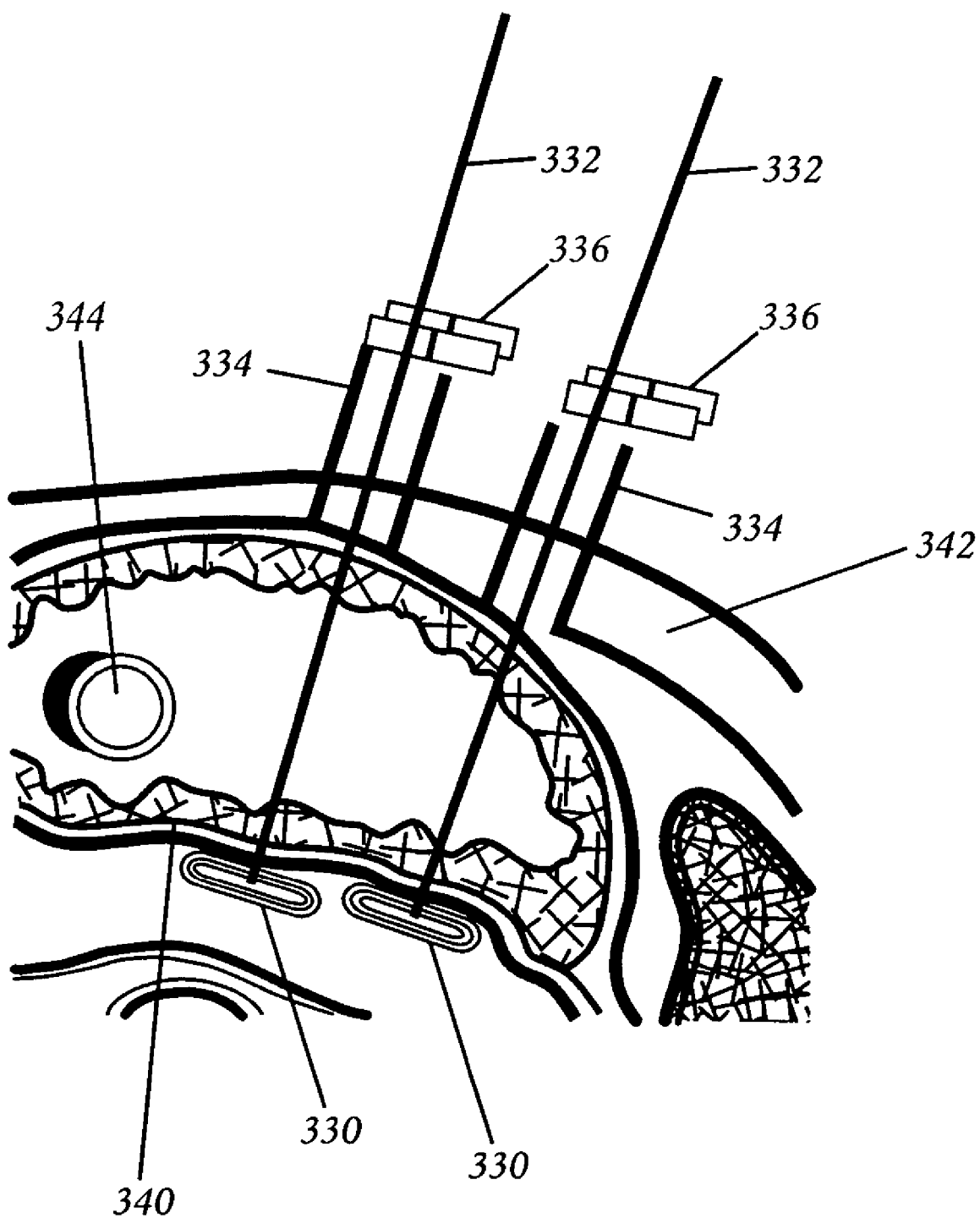
FIG. 8B shows the connectors of FIG. 8A with clamps placed on the connectors outside the patient's body to temporarily hold the connectors in a test position.

When it is desired to place more than one set of transgastric assemblies and in particular when the assemblies are placed concurrently rather than sequentially, the surgeon is afforded the opportunity to test (e.g measuring stomach volume, resistance to flow, assessing mucosal integrity, etc.) varying tensions on one or more of the fastening assemblies, all under endoscopic inspection. After the desired number of posterior anchors and connectors are deployed in the patient, the configuration of the stomach can be tested by applying tension to the connectors. FIG. 8B depicts temporary clamps 336 which sit on top of the ports 334. In some embodiments, the clamps are tensiometers which quantify the tension between the anchors. Connectors 332 can be pulled from outside the abdomen to urge the posterior wall of the stomach 340 toward the anterior abdominal wall 342. One or more clamps 336 can then be closed to hold the stomach in a test position. To determine if the posterior anchors 330 are in the desired location, an endoscope 344 can be used to view the configuration and the tension that the stomach will endure after the anterior anchors are placed.

In an alternative embodiment, the stomach is fastened to the abdominal wall rather than there being a free space between the anterior gastric wall and the peritoneum of the abdominal wall (not shown). The initial steps are as discussed above. After the posterior anchors are placed, their position can be tested as depicted in FIG. 8B to simulate the configuration after the anterior anchor is placed. Next, the outer laparoscopic port is pulled back so that the anchor deploying instrument directly contacts and sits within the tissues of the muscular abdominal wall. Once the outer laparoscopic port is pulled back, the anterior anchor can be deployed within the abdominal wall musculature and the connector can be cut flush with the anterior anchor. In an embodiment where the inflatable anterior anchor is used, after the anterior anchor is deployed within the abdominal wall musculature, the inflation tube is cut, preferably flush with the anterior anchor.

Reversal of the Gastric Volume Reduction Procedure

The connector of a preferred embodiment of the deployed transgastric fastening assembly, as illustrated in FIG. 7C, can be cut at a point between the anterior and posterior anchors, which results in reversal of the gastric volume reduction. The connector is preferably made to resist corrosion from stomach acid, but is able to be cut by a cutting implement advanced through an endoscope into the stomach. In the Smith paper (full reference above), a nylon suture was used to traverse the stomach in the anterior-posterior direction and attach the pledgets to the walls of the stomach. The nylon material was suitable for use for over 3 years without any indication of corrosion (Smith, L. et. al. Results and Complications of Gastric Partitioning. The American Journal of Surgery. Vol. 146; December 1983). Other materials suitable to prevent corrosion and yet allow cutting include plastics such as polyurethane, silicone elastomer, polypropylene, PTFE, PVDF, or polyester, metals and metal alloys such as stainless steel, nickel-titanium, titanium, cobalt-chromium, etc. Once the connector is cut, the walls of the stomach are free to move away from one another, thereby reversing the procedure. Reversal of the procedure can occur at any time (days to years) after the procedure. In a preferred embodiment, the anchors remain in the gastric wall permanently even after the connector is cut or otherwise divided. Alternatively, the anchors can in part or in whole be manufactured from a bioabsorbable material such that the anchors will eventually be absorbed by the body. In the case of bioabsorbable anchors, it is preferable to have a connector which is at least in part bioabsorbable. In another embodiment, substantially all of the elements of the transgastric fastening assembly are made of bioabsorbable materials, with the intent that over the desired period of time, the entire assembly will be absorbed by the body, reversing the procedure without any additional actions required by a doctor. In another embodiment, the anchors are made of a non-reactive material such as silicone. In this embodiment, reversal of the procedure requires a "laparoscopic procedure;" that is, pneumoperitoneum. The connector is cut with the endoscope and then the anchors are removed with standard laparoscopic instrumentation; being composed of silicone, the anchors in this case will be easily removed.

Even if there is some degree of fusion between the mucosa around the connector at the region of the assembly, once the connector is cut or absorbed, the walls will tend to move apart over time. Alternatively, a balloon or other dissection device is introduced through an endoscope and used to separate the walls of the stomach at the point of fusion.

Treatment of Disease Conditions

Figure 9:
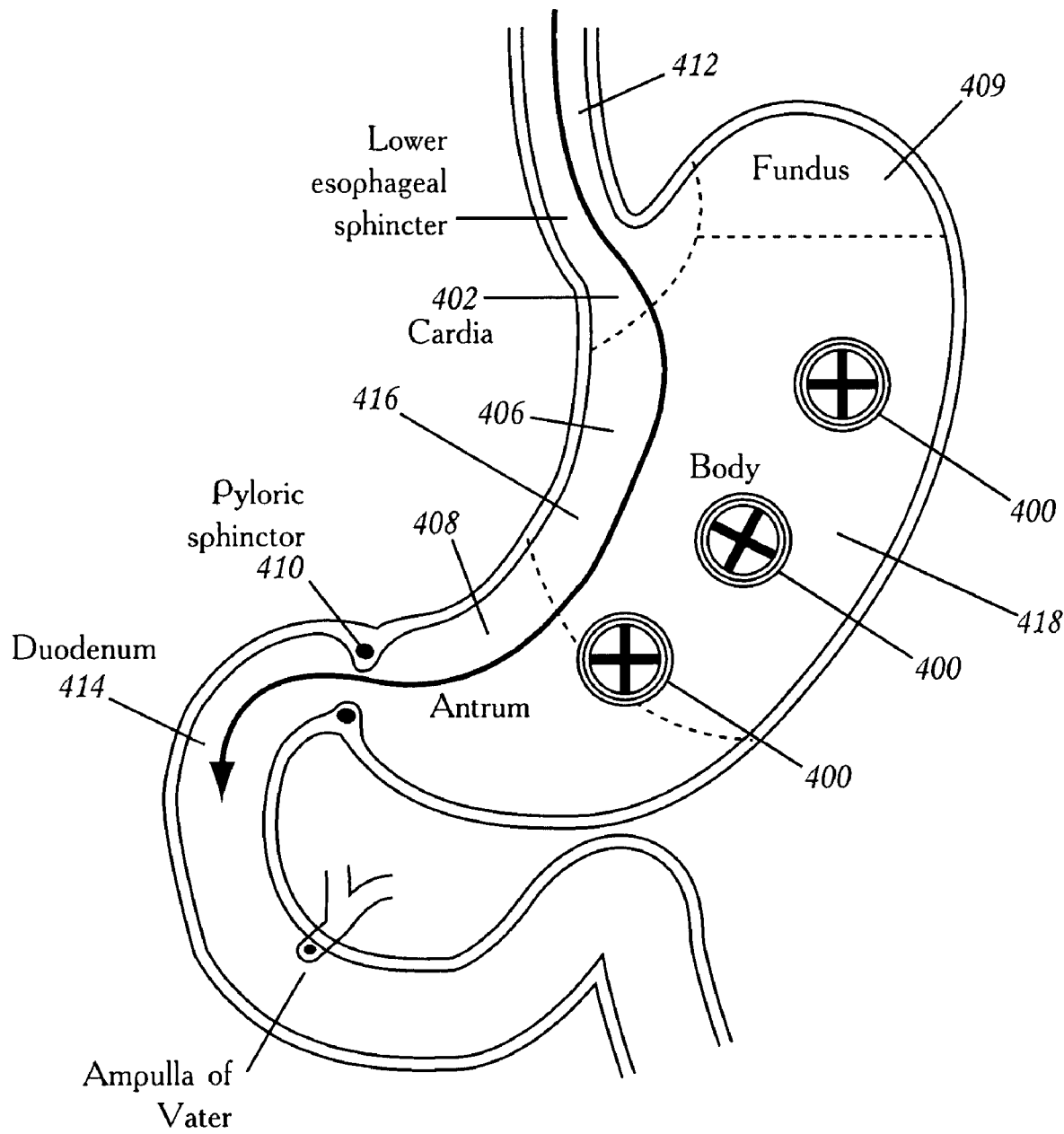
FIG. 9 is a perspective view showing three transgastric fastening assemblies deployed longitudinally in a patient's stomach.

The devices, methods and instruments disclosed above can be used to treat obesity and other diseases involving the gastrointestinal tract, such as gastroesophageal reflux disease (GERD). FIG. 9 depicts three transgastric fastening assemblies 400 deployed longitudinally in the stomach; such a configuration of anchors results in a tubular configuration of the remaining portion of the stomach The dashed lines represent boundaries of the divisions of the stomach: the cardia of the stomach 402, the fundus of the stomach 404, the body of the stomach 406, the antrum of the stomach 408, and the pyloric sphincter 410. In a preferred embodiment, the fastening assemblies are not implanted in the antrum 408 in order to maintain the normal digestion process of the stomach. Normal digestion occurs in the antrum which precedes passage of food into the duodenum. In stopping short of the antrum 408, the implants replicate the degree of volume reduction of the Magenstrasse and Mill (M&M) procedure (discussed above).

Food ingested by the patient follows a physiologic pathway for digestion depicted by the arrow in FIG. 9. It travels through the esophagus 412 and enters the cardia of the stomach 402. The food is digested in the stomach and pushed toward the duodenum 414 as chyme for further digestion. The preserved antrum 408 allows for relatively physiologic digestion and emptying into the duodenum 414 akin to the M&M procedure. With transgastric fastening assemblies 400 in place, food which leaves the esophagus 412 and enters the stomach, results in increased wall tension on the lesser curvature of the stomach 416 as the greater curvature of the stomach 418 will be restricted from the food pathway. The path of least resistance will be the path toward the pylorus 410 and duodenum 414. The increased wall tension of the stomach will result in a feeling of satiety by the patient, leading to decreased food intake and weight loss. Although three assemblies are shown in FIG. 9, there may be as few as one or as many as ten depending on the degree of volume reduction desired. Such flexibility in number of devices as well as the ability of the surgeon to tune the tension between the anterior and posterior anchors is advantageous. Such flexibility may enable, for example, reversal of a few anchors rather than all the anchors, such that the volume reduction procedure is partially reversed.

In another embodiment, a transgastric fastening assembly is placed in the antrum 408 or the region just proximal to the pyloric sphincter 410 if deemed necessary by the gastroenterologist and/or surgeon. Such a configuration would not reduce the volume of the stomach but would cause a feeling of fullness similar to a gastric outlet obstruction, leading to decreased food intake and weight loss. The anchors in this region can also conduct a current to electrically stimulate the stomach to simulate satiety.

In another embodiment, a transgastric fastening assembly may be required at the region of the cardia 402 to treat morbid obesity in a similar manner to that utilized with the LAP-BAND™ (Inamed Corp., Santa Barbara, Calif.). In this embodiment, the transgastric fastening assembly is not utilized to reduce the volume of the stomach, but to create a restriction to the inflow of food. In this embodiment, the fastening system can traverse the cardia but will not completely oppose (or at least will not prevent the flow of food through the fastening system) the mucosal surfaces of the anterior and posterior walls of the stomach.

In another embodiment, the surgeon or gastroenterologist may choose to treat a disease such as gastroesophageal reflux disease (GERD) with a transgastric fastening assembly in the cardia region. Such a configuration would maintain the position of the GE junction in the abdomen and potentially create a barrier to reflux contents.

In another embodiment, the disclosed method in combination with the transgastric fastening assemblies can be adapted to attach a gastrointestinal organ to the abdominal wall which in addition to reducing volume can also create a kink in the organ. The kink would cause a resistance barrier (in addition to volume reduction) to gastrointestinal contents, and can be useful to treat reflux disease or morbid obesity.

Such a kink would also fix the gastrointestinal region to the abdominal wall can also maintain the reduction of a hiatal hernia in the abdominal compartment (e.g. in reflux disease). A major component of reflux disease is a hiatal hernia in which the gastroesophageal junction freely slides from the abdomen to the mediastinum. A percutaneously placed suture or anchor in the region of the gastric cardia and/or fundus can tether the junction to the abdominal wall and confine the junction to the abdomen.

In other embodiments, the devices and methods of this invention can assist in the implantation of devices such as stents, meshes, stitches, or tubes in the gastrointestinal tract. The major technical difficulty encountered in placing stents, tubes, balloons, stimulators, and meshes inside the lumen of the gastrointestinal tract is that they tend to migrate because the walls of such devices do not adhere to slippery mucosa. A transgastric or transintestinal anchor, implanted with the current instrumentation could solve this problem. Such a method would be particularly useful in the attachment of the stent part of the stent-sleeve system outlined in patent application WO 04049982, or the mesh of patent application WO03086247A1. In another example, devices such as those disclosed in patent U.S. Pat. No. 6,773,441 attempt to place an endoscopic stitch to tether the cardia of the stomach to the fundus to treat reflux disease. Such stitches are tenuous in the long term because they do not necessarily penetrate the serosa. Even if the stitches penetrate the serosa, they tend to erode through the wall with time because of their thin profile and an inability of the endoscopic operator to control tension on the suture when it is placed. With the methods and devices of this invention, such an endoscopic suture can be buttressed with a percutaneously placed anchor.

Other Embodiments of the Disclosed Devices, Instruments, and Methods

Although the described methods are focused on the implantation of transgastric fastening assemblies to reduce the volume of the stomach or to increase the resistance to the flow of food in the stomach, the methods and devices can easily be expanded to the placement of other types of devices such as neurostimulators, gastric muscle stimulators, gastric balloons, and bulking devices inside the wall of a gastrointestinal organ using the percutaneous methods and devices described herein.

The methods can further be used to apply an energy source to an internal organ. For example, the methods and devices of the current invention can be used to apply radiofrequency probes, microwave probes, ultrasound probes, and radioactive probes in similar ways as disclosed in PCT WO 00/69376. The methods can further be used for diagnostic purposes prior to performing a surgical therapy. In one example, the methods and devices are used to identify specific nerves or nerve plexuses prior to a delivering a specific therapy. In another example, specific hormone producing, such as ghrelin are identified prior to delivering a specific therapy.

In one embodiment of the current invention, a neurostimulator or neurostimulator lead is placed in the serosal layer of the stomach or small intestine to stimulate the muscular or nervous portion of the stomach or small intestine (e.g. the duodenum). In some embodiments, the stimulator contacts and acts on the parasympathetic, the enteric, or the sympathetic nervous system; in other embodiments, the stimulator acts on the muscular portion of the stomach. The stimulator can be placed anywhere along the stomach including the anterior and/or posterior walls of the stomach. In some embodiments, the stimulator contacts the mucosa and in other embodiments, the stimulator does not contact the mucosa. In some embodiments, a sensor is placed as a component of the stimulator or as a separate device. In some embodiments, the stimulator further communicates with a second or third stimulator. In one embodiment, a sensor is implanted using the methods and devices described herein; the sensor can communicate with the stimulator. In one example, the sensor is placed in the stomach wall and senses stretch in the stomach. This sensor communicates with the stimulator device to create a feedback loop in which stretch is sensed (the sensor) and then a signal is sent to the stimulator portion of the system (the effecter) wherein a nerve (for example, the vagus nerve or sympathetic plexus) is stimulated to prompt the patient to slow their food intake. The effecter of the feedback loop does not have to be a nervous structure and in some embodiments is a muscular portion of the stomach or duodenum such as the pyloric channel, the antrum, the cardia, or the fundus. In some embodiments, the effecter is a patient stimulus such as a small electrical current under the skin to inform the patient, that the stomach is full. The current or effecter portion of the feedback loop can increase in intensity if the patient ignores the signal and continues to push food into the stomach cavity.

In some embodiments, the methods and devices described herein to place devices inside or outside the stomach; inside or outside the lesser sac of the peritoneum; inside or beside a structure within the retroperitoneum; inside, beside, or outside the duodenum, pylorus, or gastroesophageal junction. Implanted devices include but are not limited to the anchor devices and transgastric fastening assemblies described above, stents, meshes, stent-grafts, stitches, and bulk forming agents can be placed as well.

In one embodiment, a transgastric fastening assembly serves to reduce the volume of the stomach as well as provide for electrical stimulation. In this embodiment, an electrical signal runs through electrodes in the transgastric fastener assembly to alter the contraction patterns of the stomach or to electrically create a feeling of satiety in addition to reducing the volume of the stomach and creating a restriction to flow in the stomach. Thus, fastener assemblies of the present invention can become electrodes which are useful, for example, for gastric electrical stimulation. Methods and devices of this invention can also be used to place sutures in the stomach or pylorus to treat reflux disease or obesity. Such suturing would be facilitated by the placement of multiple ports through the walls of the stomach. Any of these methods and devices could be used in combination with or in place of the transgastric fastening assemblies to induce weight loss in a patient.

In another embodiment, the novel methods, implantation devices, and anchors of this invention are used to implant devices in one wall of a gastrointestinal organ without volume reduction. One example of such an embodiment is illustrated in FIGS. 10A and 10B in which a balloon-like device is deployed in the stomach to displace volume rather than to reduce volume from the outside. The internal balloon 430 is similar to the posterior anchors in some of the embodiments described above. In one embodiment, after initial insufflation of the stomach and placement of a laparoscopic port 306 (percutaneously and without pneumoperitoneum) between the abdominal wall 304 and the anterior wall of the stomach 302, an instrument is used to penetrate only the anterior wall of the stomach 302 and place an inflatable intragastric balloon 430. Inflation is achieved through the connector lumen 432 and the balloon is placed within the interior of the stomach 428, as illustrated in FIG. 10A. When inflated, the balloon 430 is preferably spherical in shape such that it occupies a substantial portion of the stomach volume when inflated. In the embodiment shown, the connector also acts as the inflation tube for inflating the intragastric balloon. In another embodiment, in addition to the connector, there is a separate inflation tube similar to embodiments presented above. As discussed above, a valve can be located between the anchor and the connector, or alternatively outside the patient. Preferably after the intragastric balloon is inflated and an anterior anchor 434 is deployed on the connector 432, as described previously. The connector is also cut, preferably flush with the anterior anchor, and the laparoscopic port is removed, as shown in FIG. 10B. The anchor portion of the intragastric balloon is then fixed in the wall of the stomach. In the preferred embodiment where an inflatable anterior anchor 434 is used, the inflation tube is also cut, preferably flush with the anterior anchor. Other devices which may only be implanted in one gastric wall include neurostimulators, muscular stimulators, sensors, and pharmaceutical delivery devices.

Figure 11C:
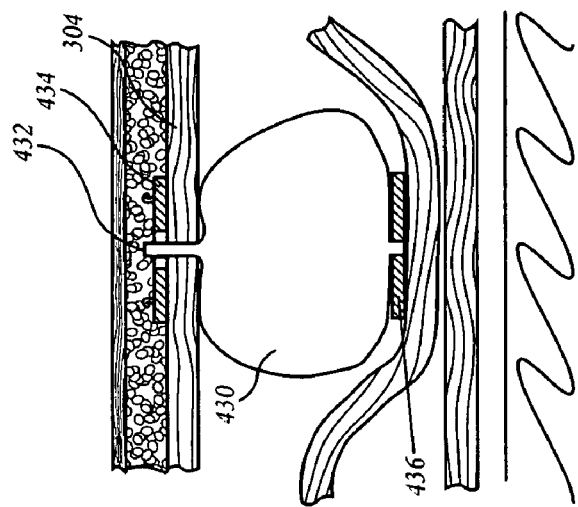
FIG. 11C illustrates a volume displacing device which resides outside the stomach and is fixed to the anterior wall of the stomach and to the abdominal wall with an anterior anchor and connector.
Figure 11B:
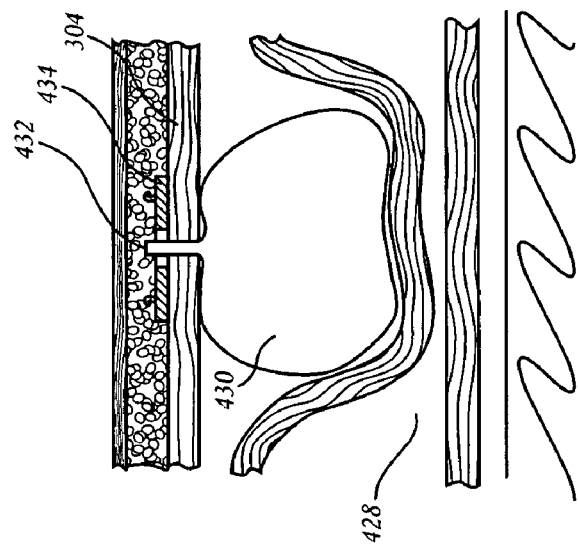
FIG. 11B illustrates a volume displacing device which resides outside that stomach and is shown in a deployed state and attached to the abdominal wall and with an anterior anchor and connector.
Figure 11A:
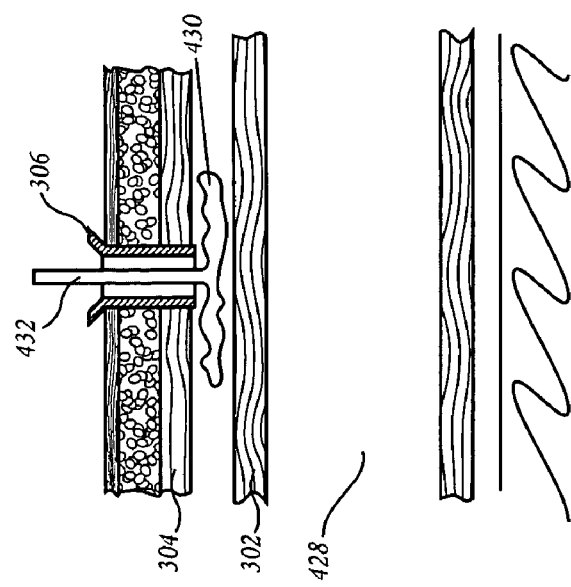
FIG. 11A illustrates a volume displacing device which resides outside the stomach and is shown in an undeployed state.

In another embodiment, an extragastric balloon is used to reduce the volume of the stomach and/or create a barrier to the flow of food and a restrictor to the flow of food. FIG. 11a depicts the balloon 430 in the undeployed configuration. The balloon is placed through a trocar port 306 which is placed in between the peritoneum and anterior wall of the stomach as described in detail above. FIG. 1B shows an embodiment of an extragastric balloon 430 in its deployed state. The balloon 430 is attached to the abdominal wall by any of the percutaneous anchor-connector assemblies and methods described above. Stem 432 is the residual from the connector used to place the balloon with an optional access port for further inflation and/or deflation after the balloon is placed. In some embodiments (FIG. 11c), the posterior portion of the balloon 436 is fixed to the outer portion or inner portion of the stomach using any of the fastening systems described above. The posterior portion of the balloon can also be fixed to the anterior gastric wall with an anchor delivered through the stomach with an endoscope. The extragastric balloon can be placed anywhere along the stomach, even at a position 1-5 cm below the gastroesophageal junction at the same place where laparoscopically placed gastric bands are currently placed. The balloon can further be shaped to circumscribe a structure such as the gastroesophageal junction.

FIG. 18 embodies another use for the current invention. The sleeve device 620 is disclosed in U.S. patent application publication U.S. 2004/02206882. A major difficulty with this sleeve device is that it is not easily fixtured for stability inside the stomach. Fastening system 610 is used to assist in fixation of the device 620 to the stomach wall; fastening system 610 is any of the devices discussed above and is implanted by any of the methods discussed above.

In another embodiment, a surgical anastomosis is surrounded with the organ spanning anchors and anchor assemblies of the current invention. In this embodiment, the anchors can buttress the anastomosis to protect the integrity of the anastomosis. The buttresses support both the hand-sewn and the stapler anastomotic techniques. To prevent or support leaks, the anchors are placed around or through the anastomosis.

The anchors can also be used to control the flow of material through the anastomosis. Flow control is attainable when two anchors are applied across an anastomosis and are linked by means of a connector through the anastomosis. The distance between the anchors determines the amount of flow through the anastomosis and therefore, the flow rate can be adjusted quite readily with the device of the current invention. The flow rate is adjustable at anytime during or after the operation. Luminal devices to control the flow rate through an anastomosis can be found in patent application number 20050022827. The devices of the current invention can be used to accomplish the goal of controlling flow through an anastomosis by placing anchors that traverse the anastomosis. In other embodiments, the anchors of the current invention can be used to secure the luminal devices in patent application number 20050022827.

In another embodiment, the anchor assemblies are applied to the lung to treat chronic obstructive pulmonary disease (COPD) via functional lung reduction. Rather than removing a portion of the lung (the surgical procedure), the anchors of the current invention are placed through the diseased portion of the lung to close off or at least create a large resistance in one portion of the lung and broncheoalveolar tree so that inspired air does not reach a malfunctioning portion of the lung.

Similarly, the anchor assemblies and anchors are applied to other solid organs such as the spleen, kidney, liver, and pancreas to urge the edges of a defect together to promote healing.

In other embodiments of the current invention, the fastening systems and tools to implant the fastening systems are used to secure closure or repair of blood vessels. The blood vessels can be named vessels such as the aorta, vena cava, pulmonary veins, pulmonary arteries, renal vein, renal artery, inferior mesenteric vein and/or artery, splenic vein and/or artery, portal vein and/or hepatic artery. Alternatively, the vessels are unnamed such as in the case of the mesentery of the colon or small bowel. Vessel closure with the current system is possibly more efficient than current laparoscopic means of vessel closure which involve staple or clip occlusion of the vessels; however, staples and clips are often inadequate because they do not penetrate the vessel to create occlusion and therefore are often inadequate, or at least do not replicate what a surgeon would do in an open procedure.

It is also possible that a part of, or any or all of the devices and methods described above are performed with an alternative imaging means; for example, fluoroscope, MRI, CAT scan.

Although the present invention has been described in the context of certain preferred or illustrative embodiments, it should be understood that the scope of the exclusive right granted by this patent is not limited to those embodiments, but instead is the full lawful scope of the appended claims.

What is claimed is:

1. A method for treating a patient comprising,
   passing a first anchor through the skin of a patient;
   positioning the first anchor adjacent to the posterior wall of the stomach;
   passing at least one connector through the patient's skin and thence at least partially through the patient's anterior and posterior stomach walls;
   contacting the first anchor and the at least one connector;
   passing a second anchor at least partially through the skin of a patient's abdominal wall;
   connecting the first and second anchors by means of the at least one connector;
   urging the first and second anchors toward each other; and
   fixing the anterior and posterior walls of the stomach in the urged position with said first and second anchors.

2. The method of claim 1, wherein said second anchor is deployed within the peritoneal cavity.

3. The method of claim 1, wherein said second anchor is deployed between the abdominal skin and the outermost peritoneum of the abdominal cavity.

4. The method of claim 1, wherein passing said first anchor at least partially through the patient's abdominal skin is done while said first anchor is in a reduced profile configuration, further comprising said first anchor subsequently being in a deployed configuration.

5. The method of claim 4, wherein said reduced profile configuration of said first anchor is substantially folded, and/or compressed, and/or uninflated, and said deployed configuration is substantially unfolded and/or uncompressed and/or inflated.

6. The method of claim 1 further comprising, repeating the steps of claim 7 for additional anchors in the same organ.

7. The method of claim 1, wherein said urging does not completely bring said anterior and posterior walls of the stomach together.

8. The method of claim 1 wherein said urging brings said anterior and posterior wall of the stomach together.

9. The method of claim 1, further comprising delivering an electrical signal to said anterior stomach wall through said second anchor.

10. The method of claim 1, further comprising delivering an electrical signal to said posterior stomach wall through said first anchor.

11. The method of claim 1, wherein said connector comprises a force sensor.

12. The method of claim 1, further comprising placing a balloon between the first and second anchors to fix the balloon between the anterior and posterior stomach walls.

13. The method of claim 1, further comprising placing a food shunt between the first and second anchors to fix the food shunt between the first and second stomach walls.

14. The method of claim 1, further comprising detecting a force signal applied to the connector and providing a signal to the patient as to the magnitude of the force.

15. The method of claim 14, wherein said signal is cutaneous stimulation.

16. The method of claim 1 wherein the first anchor is deployed within the stomach.

17. A method for implanting a stomach traversing device in a patient, comprising:
    placing a first surgical instrument adjacent to the posterior wall of the stomach;
    passing a first end of a second surgical instrument through a patient's skin, through the anterior wall of the stomach, through the interior of the stomach, and thence through the posterior wall of the stomach, so that the second surgical instrument traverses the stomach;
    contacting the first surgical instrument with the second surgical instrument;
    deploying a first anchor from the first surgical instrument wherein the first anchor is located adjacent to the posterior wall of the stomach;
    deploying a second anchor within the patient;
    providing at least one connector wherein the connector contacts the first anchor, and the second anchor;
    stabilizing the first and second anchors and the at least one connector by engaging the at least one connector with the first and second anchors.

18. The method of claim 17, further comprising adjusting the length of said connector between said anterior and said posterior walls of the stomach after implantation of said organ traversing anchors is finished.

* * * * *